(12) United States Patent
Shimada et al.

(10) Patent No.: US 10,975,070 B2
(45) Date of Patent: Apr. 13, 2021

(54) GHRELIN RECEPTOR AGONIST FOR TREATMENT OF CACHEXIA

(75) Inventors: Kaoru Shimada, Aichi (JP); Masaki Sudo, Aichi (JP); Masaomi Tajimi, Aichi (JP); Nobuyuki Takahashi, Aichi (JP); Kazuhiko Nonomura, Shizuoka (JP)

(73) Assignee: RaQualia Pharma Inc., Aichi (JP)

( * ) Notice: Subject to any disclaimer, the term of this patent is extended or adjusted under 35 U.S.C. 154(b) by 0 days.

(21) Appl. No.: 13/580,479

(22) PCT Filed: Feb. 28, 2011

(86) PCT No.: PCT/JP2011/054556
§ 371 (c)(1),
(2), (4) Date: Aug. 30, 2012

(87) PCT Pub. No.: WO2011/105611
PCT Pub. Date: Sep. 1, 2011

(65) Prior Publication Data
US 2012/0322821 A1    Dec. 20, 2012

(30) Foreign Application Priority Data
Feb. 26, 2010 (JP) .............................. JP2010-043484

(51) Int. Cl.
    A61K 31/44    (2006.01)
    C07D 471/04   (2006.01)
    A61K 31/437   (2006.01)
    A61K 45/06    (2006.01)

(52) U.S. Cl.
    CPC .......... *C07D 471/04* (2013.01); *A61K 31/437* (2013.01); *A61K 45/06* (2013.01)

(58) Field of Classification Search
    CPC . A61K 31/437; A61K 2300/00; C07D 471/04
    See application file for complete search history.

(56) References Cited

U.S. PATENT DOCUMENTS

| 6,107,306 A | 8/2000 | Carpino |
| 2002/0042419 A1 | 4/2002 | Hakkinen |
| 2008/0261873 A1 | 10/2008 | Geesaman |
| 2010/0069431 A1 | 3/2010 | Iwata et al. |
| 2014/0088139 A1 | 3/2014 | Zollers et al. |

FOREIGN PATENT DOCUMENTS

| EP | 1159964 A2 | | 12/2001 |
| EP | 1186293 | * | 3/2002 |
| JP | 11501945 A | | 2/1999 |
| JP | 2002012556 A | | 1/2002 |
| JP | 2007063225 A | | 3/2007 |
| JP | 2008510706 A | | 4/2008 |
| WO | WO-9724369 A1 | | 7/1997 |
| WO | WO-2006023608 A2 | | 3/2006 |
| WO | WO2008100448 | * | 8/2008 |
| WO | WO-2008153027 A1 | | 12/2008 |
| WO | WO-2009063993 A1 | | 5/2009 |
| WO | WO-2009139340 A1 | | 11/2009 |

OTHER PUBLICATIONS

DeBoer et al., Endocrinology, Jun. 2007, 148 (6), pp. 3004-3012.*
International Preliminary Report on Patentability in corresponding PCT/JP2011/054556 dated Sep. 4, 2012.
Carpino et al., "Discovery and Biological Characterization of Capromorelin Analogues with Extended Half-Lives," *Bioorganic & Medicinal Chemistry Letters*, 12:3279-3282 (2002).
Garcia et al., "Active Ghrelin Levels and Active to Total Ghrelin Ratio in Cancer-Induced Cachexia," *Journal of Clinical Endocrinology and Metabolism*, 90(5):2920-2926 (2005).
Supplementary European Search Report for European Patent Application No. 11 74 7565 dated Jun. 26, 2013.
International Search Report in corresponding PCT/JP2011/054556 dated May 17, 2011.
Written Opinion in corresponding PCT/JP2011/054556 dated May 17, 2011 (Japanese only).
Kern et al., "Cancer Cachexia," *J. Parenteral and Enteral Nutrition* 12:286-298, 1988.
Lahdevirta et al., "Elevated Levels of Circulating Cachectin/Tumor Necrosis Factor in Patients with Acquired Immunodeficiency Syndrome," *The American Journal of Medicine* 85: 289-291, 1988.
Nelson et al., "The Cancer Anorexia-Cachexia Syndrome," *Journal of Clinical Oncology* 12(1): 213-225, Jan. 1994.
Fraser et al., "Effect of the ghrelin receptor agonist TZP-101 on colonic transit in a rat model of postoperative ileus", European Journal of Pharmacology, vol. 604, pp. 132-137 (2009).

* cited by examiner

*Primary Examiner* — Shobha Kantamneni
(74) *Attorney, Agent, or Firm* — Wenderoth, Lind & Ponack, L.L.P.

(57) ABSTRACT

The present invention relates to use of a compound of the present invention or a pharmaceutically acceptable salt thereof, or a pharmaceutical composition comprising the compound or the salt, for the manufacture of a medicament for the treatment of cachexia. The invention also relates to a method for the treatment of cachexia, comprising administering the compound of the present invention or a pharmaceutical composition comprising the same to a human or an animal. The invention further relates to use of said compound, or a pharmaceutically acceptable salt thereof, or a pharmaceutical composition comprising the compound or the salt, in combination with one or more second active agents. Moreover, the invention relates to a pharmaceutical composition and a kit comprising the compound of the present invention or a pharmaceutically acceptable salt thereof, for the treatment of said disease.

8 Claims, No Drawings

GHRELIN RECEPTOR AGONIST FOR TREATMENT OF CACHEXIA

TECHNICAL FIELD

The present invention relates to a therapeutic agent for cachexia which develops in chronic diseases such as malignant tumor, tuberculosis, diabetes, hemodyscrasia, endocrine disease, chronic obstructive pulmonary disease, chronic kidney disease, cardiac failure, infectious disease, and acquired immunodeficiency syndrome. Particularly, this invention relates to use of a compound which has agonistic activity against the ghrelin receptor, which promotes growth hormone secretion, and is represented by the following general formula (I), or a pharmaceutically acceptable salt thereof, or a pharmaceutical composition comprising the compound or the salt, for the manufacture of a medicament for the treatment of cachexia. The invention also relates to a method for the treatment of cachexia, comprising administering the compound of the present invention or a pharmaceutical composition comprising the same to a human or an animal. The invention further relates to use of the said compound, or a pharmaceutically acceptable salt thereof, or a pharmaceutical composition comprising the compound or the salt, in combination with one or more second active agents. Moreover, the invention relates to a pharmaceutical composition or a kit comprising the compound of the following general formula (I) or a pharmaceutically acceptable salt thereof, for the treatment of said diseases.

(I)

{Chem. 1}

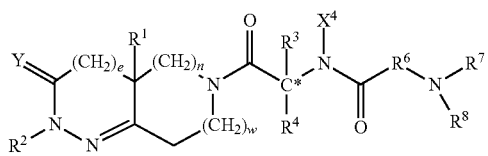

BACKGROUND ART

Cachexia is a systemic syndrome which is associated with progressive loss of body weight, anemia, edema, and anorexia as cardinal symptoms and which develops in chronic diseases such as malignant tumor, tuberculosis, diabetes, hemodyscrasia, endocrine disease, chronic obstructive pulmonary disease, chronic kidney disease, cardiac failure, infectious disease, and acquired immunodeficiency syndrome [e.g. Kern et al., Cancer Cachexia, J. Parenteral and Enteral Nutrition, 12, 286-298 (1988) and American Journal of Medicine, 85, 289-291 (1988)]. In cachexia, therapeutic nutrition and endocrine therapy are generally administered but a satisfactory anticachectic modality remains to be established. Particularly where cachexia is caused by a malignant tumor, the available anticancer chemotherapy cannot be administered when cachexia is progressing, with the result that the treatment encounters a serious setback. Moreover, any therapeutic nutrition for relief of cachectic symptoms may rather exacerbate the malignant tumor and detract from the life expectancy of the patient. While cachexia is frequently caused by the malignant tumors, administration of an antitumor agent in such settings may result in control of the tumors but generally side effects of the drug develop in superimposition, the net result being no improvement in cachexia [Nelson et al., Journal of Clinical Oncology, 12, 213-225 (1994)].

CITATION LIST

Non-Patent Literature

{Non-Patent Literature 1}
Kern et al., "Cancer Cachexia".
{Non-Patent Literature 2}
J. Parenteral and Enteral Nutrition, 12, 286-298 (1988).
{Non-Patent Literature 3}
American Journal of Medicine, 85, 289-291 (1988).
{Non-Patent Literature 4}
Nelson et al., Journal of Clinical Oncology, 12, 213-225 (1994).

SUMMARY OF INVENTION

Technical Problem

Under the circumstances mentioned in the background art, there is a need for a therapeutic agent that can ameliorate or inhibit the progression of cachectic symptoms such as loss of body weight.

Solution to Problem

The gist of the present invention is as follows:

[1] A use of one or more selected from the group consisting of a compound of the formula (I), a racemic-diastereomeric mixture and an optical isomer of said compound, and a pharmaceutically acceptable salt and a prodrug thereof, for the manufacture of a medicament for the treatment of cachexia in a human or an animal:

(I)

{Chem. 2}

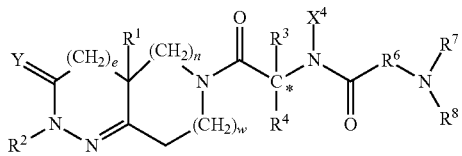

wherein
e is 0 or 1;
n and w are each independently 0, 1 or 2, provided that w and n cannot both be 0 at the same time;
Y is oxygen or sulfur;
$R^1$ is hydrogen, —CN, —$(CH_2)_q N(X^6)C(O)X^6$, —$(CH_2)_q N(X^6)C(O)(CH_2)_t$-$A^1$, —$(CH_2)_q N(X^6)SO_2(CH_2)_t$-$A^1$, —$(CH_2)_q N(X^6)SO_2 X^6$, —$(CH_2)_q N(X^6)C(O)N(X^6)(CH_2)_t$-$A^1$, —$(CH_2)_q N(X^6)C(O)N(X^6)(X^6)$, —$(CH_2)_q C(O)N(X^6)(X^6)$, —$(CH_2)_q C(O)N(X^6)(CH_2)_t$-$A^1$, —$(CH_2)_q C(O)OX^6$, —$(CH_2)_q C(O)O(CH_2)_t$-$A^1$, —$(CH_2)_q OX^6$, —$(CH_2)_q OC(O) X^6$, —$(CH_2)_q OC(O)(CH_2)_t$-$A^1$, —$(CH_2)_q OC(O)N(X^6)(CH_2)_t$-$A^1$, —$(CH_2)_q OC(O)N(X^6)C(O)OX^6)$, —$(CH_2)_q C(O)X^6$, —$(CH_2)_q C(O)(CH_2)_t$-$A^1$, —$(CH_2)_q N(X^6)C(O)OX^6$, —$(CH_2)_q N(X^6)SO_2 N(X^6)(X^6)$, —$(CH_2)_q S(O)_m X^6$, —$(CH_2)_q S(O)_m(CH_2)_t$-$A^1$, —$(C_1$-$C_{10})$alkyl, —$(CH_2)_t$-$A^1$, —$(CH_2)_q$—$(C_3$-$C_7)$cycloalkyl, —$(CH_2)_q$—$Y^1$—$(C_1$-$C_5)$alkyl, —$(CH_2)_q$—$Y^1$—$(CH_2)_t$- $A^1$ or —$(CH_2)_q$—$Y^1$—$(CH_2)_t$—$(C_3$-$C_7)$cycloalkyl (where the alkyl and cycloalkyl groups in the definition of $R^1$ are optionally substituted with $(C_1-C_4)$alkyl, hydroxyl, $(C_1-C_4)$alkoxy, carboxyl, —$CONH_2$, —$S(O)_m(C_1-C_6)$alkyl, —$CO_2(C_1-C_4)$alkyl ester, 1H-tetrazol-5-yl or 1, 2 or 3 fluoro;

$Y^1$ is O, $S(O)_m$, —$C(O)NX^6$—, —CH=CH—, —C≡C—, —$N(X^6)C(O)$—, —$C(O)NX^6$—, —$C(O)O$—, —$OC(O)N(X^6)$— or —$OC(O)$—;

q is 0, 1, 2, 3 or 4;

t is 0, 1, 2 or 3;

said $(CH_2)_q$ group and $(CH_2)_t$ group may each be optionally substituted with hydroxyl, $(C_1-C_4)$alkoxy, carboxyl, —$CONH_2$, —$S(O)_m(C_1-C_6)$alkyl, —$CO_2(C_1-C_4)$alkyl ester, 1H-tetrazol-5-yl, 1, 2 or 3 fluoro, or 1 or 2 $(C_1-C_4)$alkyl);

$R^2$ is hydrogen, $(C_1-C_8)$alkyl, —$(C_0-C_3)$alkyl-$(C_3-C_8)$cycloalkyl, —$(C_1-C_4)$alkyl-$A^1$ or $A^1$ (where the alkyl groups and cycloalkyl groups in the definition of $R^2$ are optionally substituted with hydroxyl, —$C(O)OX^6$, —$C(O)N(X^6)(X^6)$, —$N(X^6)(X^6)$, —$S(O)_m(C_1-C_6)$alkyl, —$C(O)A^1$, —$C(O)(X^6)$, $CF_3$, CN or 1, 2 or 3 halogen);

$R^3$ is $A^1$, $(C_1-C_{10})$alkyl, —$(C_1-C_6)$alkyl-$A^1$, —$(C_1-C_6)$alkyl-$(C_3-C_7)$cycloalkyl, —$(C_1-C_5)$alkyl-$X^1$—$(C_1-C_5)$alkyl, —$(C_1-C_5)$alkyl-$X^1$—$(C_0-C_5)$alkyl-$A^1$ or —$(C_1-C_5)$alkyl-$X^1$—$(C_1-C_5)$alkyl-$(C_3-C_7)$cycloalkyl (where the alkyl groups in the definition of $R^3$ are optionally substituted with —$S(O)_m(C_1-C_6)$alkyl, —$C(O)OX^3$, 1, 2, 3, 4 or 5 halogen, or 1, 2 or 3 $OX^3$;

$X^1$ is O, $S(O)_m$, —$N(X^2)C(O)$—, —$C(O)N(X^2)$—, —OC(O)—, —$C(O)O$—, —$CX^2=CX^2$—, —$N(X^2)C(O)O$—, —$OC(O)N(X^2)$— or —C≡C—);

$R^4$ is hydrogen, $(C_1-C_6)$alkyl or $(C_3-C_7)$cycloalkyl, or $R^4$ is taken together with $R^3$ and the carbon atom to which they are attached and form $(C_5-C_7)$cycloalkyl, $(C_5-C_7)$cycloalkenyl, a partially saturated or fully saturated 4- to 8-membered ring having 1 to 4 heteroatoms independently selected from the group consisting of oxygen, sulfur and nitrogen, or is a bicyclic ring system consisting of a partially saturated or fully saturated 5- or 6-membered ring, fused to a partially saturated, fully unsaturated or fully saturated 5- or 6-membered ring, optionally having 1 to 4 heteroatoms independently selected from the group consisting of nitrogen, sulfur and oxygen;

$X^4$ is hydrogen or $(C_1-C_6)$alkyl or $X^4$ is taken together with $R^4$ and the nitrogen atom to which $X^4$ is attached and the carbon atom to which $R^4$ is attached and form a five to seven membered ring;

$R^6$ is a bond or is

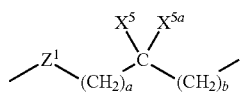

{Chem. 3}

(where a and b are independently 0, 1, 2 or 3;

$X^5$ and $X^{5a}$ are each independently selected from the group consisting of hydrogen, trifluoromethyl, $A^1$ and optionally substituted $(C_1-C_6)$alkyl;

the optionally substituted $(C_1-C_6)$alkyl in the definition of $X^5$ and $X^{5a}$ is optionally substituted with a substituent selected from the group consisting of $A^1$, $OX^2$, —$S(O)_m(C_1-C_6)$alkyl, —$C(O)OX^2$, $(C_3-C_7)$cycloalkyl, —$N(X^2)(X^2)$ and —$C(O)N(X^2)(X^2)$; or the carbon bearing $X^5$ or $X^{5a}$ forms one or two alkylene bridges with the nitrogen atom bearing $R^7$ and $R^8$ wherein each alkylene bridge contains 1 to 5 carbon atoms, provided that when one alkylene bridge is formed then $X^5$ or $X^{52}$ but not both may be on the carbon atom and $R^7$ or $R^8$ but not both may be on the nitrogen atom and further provided that when two alkylene bridges are formed then $X^5$ and $X^{5a}$ cannot be on the carbon atom and $R^7$ and $R^8$ cannot be on the nitrogen atom; or $X^5$ is taken together with $X^{5a}$ and the carbon atom to which they are attached and form a partially saturated or fully saturated 3- to 7-membered ring, or a partially saturated or fully saturated 4- to 8-membered ring having 1 to 4 heteroatoms independently selected from the group consisting of oxygen, sulfur and nitrogen, or $X^5$ is taken together with $X^{5a}$ and the carbon atom to which they are attached and form a bicyclic ring system consisting of a partially saturated or fully saturated 5- or 6-membered ring, optionally having 1 or 2 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;

$Z^1$ is a bond, O or N—$X^2$, provided that when a and b are both 0 then $Z^1$ is not N—$X^2$ or O);

$R^7$ and $R^8$ are independently hydrogen or optionally substituted $(C_1-C_6)$alkyl (where the optionally substituted $(C_1-C_6)$ alkyl in the definition of $R^7$ and $R^8$ is optionally independently substituted with $A^1$, —$C(O)O$—$(C_1-C_6)$alkyl, —$S(O)_m(C_1-C_6)$allyl, 1 to 5 halogen, 1 to 3 hydroxy, 1 to 3-O—$C(O)(C_1-C_{10})$alkyl or 1 to 3 $(C_1-C_6)$alkoxy); or $R^7$ and $R^8$ can be taken together to form —$(CH_2)_r$-L-$(CH_2)_r$—; where L is $C(X^2)(X^2)$, $S(O)_m$ or $N(X^2)$;

$A^1$ for each occurrence is independently $(C_5-C_7)$cycloalkenyl, phenyl or a partially saturated, fully saturated or fully unsaturated 4- to 8-membered ring optionally having 1 to 4 heteroatoms independently selected from the group consisting of oxygen, sulfur and nitrogen, a bicyclic ring system consisting of a partially saturated, fully unsaturated or fully saturated 5- or 6-membered ring, optionally having 1 to 4 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen; $A^1$ for each occurrence is independently optionally substituted, in one or optionally both rings if $A^1$ is a bicyclic ring system, with up to three substituents, each substituent independently selected from the group consisting of F, Cl, Br, I, $OCF_3$, $OCF_2H$, $CF_3$, $CH_3$, $OCH_3$, —$OX^6$, —$C(O)N(X^6)(X^6)$, —$C(O)OX^6$, oxo, $(C_1-C_6)$alkyl, nitro, cyano, benzyl, —$S(O)_m(C_1-C_6)$alkyl, 1H-tetrazol-5-yl, phenyl, phenoxy, phenylalkyloxy, halophenyl, methylenedioxy, —$N(X^6)(X^6)$, —$N(X^6)C(O)(X^6)$, —$SO_2N(X^6)(X^6)$, —$N(X^6)SO_2$-phenyl, —$N(X^6)SO_2X^6$, —$CONX^{11}X^{12}$, —$SO_2NX^{11}X^{12}$, —$NX^6SO_2X^{12}$, —$NX^6CONX^{11}X^{12}$, —$NX^6SO_2NX^{11}X^{12}$, —$NX^6C(O)X^{12}$, imidazolyl, thiazolyl and tetrazolyl, provided that if $A^1$ is optionally substituted with methylenedioxy then it can only be substituted with one methylenedioxy (where $X^{11}$ is hydrogen or optionally substituted $(C_1-C_6)$ alkyl;

the optionally substituted $(C_1-C_6)$alkyl defined for $X^{11}$ is optionally independently substituted with phenyl, phenoxy, $(C_1-C_6)$alkoxycarbonyl, —$S(O)_m(C_1-C_6)$alkyl, 1 to 5 halogen, 1 to 3 hydroxy, 1 to 3 $(C_1-C_{10})$alkanoyloxy or 1 to 3 $(C_1-C_6)$alkoxy;

$X^{12}$ is hydrogen, $(C_1-C_6)$alkyl, phenyl, thiazolyl, imidazolyl, furyl or thienyl, provided that when $X^{12}$ is not hydrogen, $X^{12}$ is optionally substituted with one to three substituents independently selected from the group consisting of Cl, F, $CH_3$, $OCH_3$, $OCF_3$ and $CF_3$;

or $X^{11}$ and $X^{12}$ are taken together to form $—(CH_2)_r-L^1-(CH_2)_r—$;

where $L^1$ is $C(X^2)(X^2)$, O, $S(O)_m$ or $N(X^2)$);

r for each occurrence is independently 1, 2 or 3;

$X^2$ for each occurrence is independently hydrogen, optionally substituted $(C_1-C_6)$allyl, or optionally substituted $(C_3-C_7)$cycloalkyl, where the optionally substituted $(C_1-C_6)$alkyl and optionally substituted $(C_3-C_7)$cycloalkyl in the definition of $X^2$ are optionally independently substituted with $—S(O)_m(C_1-C_6)$alkyl, $—C(O)OX^3$, 1 to 5 halogen or 1 to 3 $OX^3$;

$X^3$ for each occurrence is independently hydrogen or $(C_1-C_6)$alkyl;

$X^6$ is independently hydrogen, optionally substituted $(C_1-C_6)$alkyl, $(C_2-C_6)$halogenated alkyl, optionally substituted $(C_3-C_7)$cycloalkyl, $(C_3-C_7)$-halogenated cycloalkyl, where optionally substituted $(C_1-C_6)$alkyl and optionally substituted $(C_3-C_7)$cycloalkyl in the definition of $X^6$ is optionally independently substituted with 1 or 2 $(C_1-C_4)$alkyl, hydroxyl, $(C_1-C_4)$alkoxy, carboxyl, $CONH_2$, $—S(O)_m(C_1-C_6)$alkyl, carboxylate, $(C_1-C_4)$alkyl ester, or 1H-tetrazol-5-yl; or when there are two $X^6$ groups on one atom and both $X^6$ are independently $(C_1-C_6)$alkyl, the two $(C_1-C_6)$alkyl groups may be optionally joined and, together with the atom to which the two $X^6$ groups are attached, form a 4- to 9-membered ring optionally having oxygen, sulfur or $NX^7$;

$X^7$ is hydrogen or $(C_1-C_6)$alkyl optionally substituted with hydroxyl; and m for each occurrence is independently 0, 1 or 2;

with the proviso that:

$X^6$ and $X^{12}$ cannot be hydrogen when it is attached to C(O) or $SO_2$ in the form $C(O)X^6$, $C(O)X^{12}$, $SO_2X^6$ or $SO_2X^{12}$; and when $R^6$ is a bond then L is $N(X^2)$ and each r in the definition $—(CH_2)_r-L-(CH_2)_r—$ is independently 2 or 3;

[2] A use of one or more selected from the group consisting of a compound of the formula (II), a racemic-diastereomeric mixture and an optical isomer of said compound, and a pharmaceutically acceptable salt and a prodrug thereof, for the manufacture of a medicament for the treatment of cachexia in a human or an animal:

(II)

{Chem. 4}

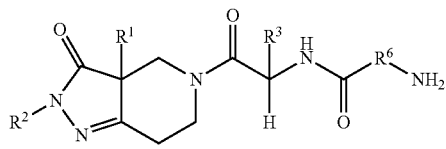

wherein $R^1$ is $—(C_1-C_3)$alkyl-phenyl, $—(C_1-C_3)$alkyl-pyridyl, $—(C_1-C_3)$alkyl-quinolinyl or $—(C_1-C_3)$alkyl-thiazolyl, where the phenyl in $R^1$ is optionally substituted with one or two substituents selected from the group consisting of halo, $CF_3$, $CH_3$ and phenyl;

$R^2$ is $—(C_1-C_4)$alkyl or $—(C_1-C_4)$alkyl-$CF_3$;

$R^3$ is $—(C_1-C_4)$alkylindolyl, $(C_1-C_4)$alkylphenyl, $—(C_1-C_4)$alkyl-O—$(C_1-C_4)$alkyl-Ar, $—(C_1-C_4)$alkyl-S—$(C_1-C_4)$alkyl-Ar, where Ar is phenyl, thienyl, thiazolyl, pyridyl, pyrimidinyl or benzisoxazolyl, said Ar is optionally substituted with one or two substituents selected from the group consisting of halo, $OCF_3$, $CF_3$ and $CH_3$; and $R^6$ is $—C(X^5)(X^5)$, where $X^5$ is $—(C_1-C_6)$alkyl;

[3] The use according to [1] or [2], wherein the compound is selected from the group consisting of the following compounds:

2-amino-N-(1-(3a-(R,S)-benzyl-2-methyl-3-oxo-2,3,3a,4,6,7-hexahydro-pyrazolo[4,3-c]pyridine-5-carbonyl)-4-phenyl(R)-butyl]-isobutyramide;

2-amino-N-(1-(3a-(R)-benzyl-2-methyl-3-oxo-2,3,3a,4,6,7-hexahydro-pyrazolo[4,3-c]pyridine-5-carbonyl)-4-phenyl(R)-butyl]-isobutyramide;

2-amino-N-(1-(3a-(S)-benzyl-2-methyl-3-oxo-2,3,3a,4,6,7-hexahydro-pyrazolo[4,3-c]pyridine-5-carbonyl)-4-phenyl(R)-butyl]-isobutyramide;

2-amino-N-[2-(3a-(R,S)-benzyl-2-methyl-3-oxo-2,3,3a,4,6,7-hexahydro-pyrazolo[4,3-c]pyridin-5-yl)-1-(R)-(1H-indol-3-ylmethyl)-2-oxo-ethyl]-isobutyramide;

2-amino-N-[2-(3a-(R)-benzyl-2-methyl-3-oxo-2,3,3a,4,6,7-hexahydro-pyrazolo[4,3-c]pyridin-5-yl)-1-(R)-(1H-indol-3-ylmethyl)-2-oxo-ethyl]-isobutyramide;

2-amino-N-[2-(3a-(S)-benzyl-2-methyl-3-oxo-2,3,3a,4,6,7-hexa hydro-pyrazolo[4,3-c]pyridin-5-yl)-1-(R)-(1H-indol-3-ylmethyl)-2-oxo-ethyl]isobutyramide;

2-amino-N-[2-(3a-(R,S)-benzyl-2-ethyl-3-oxo-2,3,3a,4,6,7-hexahydro-pyrazolo[4,3-c]pyridin-5-yl)-1-(R)-(1H-indol-3-ylmethyl)-2-oxo-ethyl]-isobutyramide;

2-amino-N-[2-(3a-(R)-benzyl-2-ethyl-3-oxo-2,3,3a,4,6,7-hexahydro-pyrazolo[4,3-c]pyridin-5-yl)-1-(R)-(1H-indol-3-ylmethyl)-2-oxo-ethyl]-isobutyramide;

2-amino-N-[2-(3a-(S)-benzyl-2-ethyl-3-oxo-2,3,3a,4,6,7-hexahydro-pyrazolo[4,3-c]pyridin-5-yl)-1-(R)-(1H-indol-3-ylmethyl)-2-oxo-ethyl]-isobutyramide;

2-amino-N-[2-(3a-(R,S)-(4-fluoro-benzyl)-2-methyl-3-oxo-2,3,3a,4,6,7-hexahydro-pyrazolo[4,3-c]pyridin-5-yl)-1-(R)-(1H-indol-3-ylmethyl)-2-oxo-ethyl]-isobutyramide;

2-amino-N-[2-(3a-(R)-(4-fluoro-benzyl)-2-methyl-3-oxo-2,3,3a,4,6,7-hexahydro-pyrazolo[4,3-c]pyridin-5-yl)-1-(R)-(1H-indol-3-ylmethyl)-2-oxo-ethyl]-isobutyramide;

2-amino-N-[2-(3a-(S)-(4-fluoro-benzyl)-2-methyl-3-oxo-2,3,3a,4,6,7-hexahydro-pyrazolo[4,3-c]pyridin-5-yl)-1-(R)-(1H-indol-3-ylmethyl)-2-oxo-ethyl]-isobutyramide;

2-amino-N-[2-(3a-(R,S)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide;

2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide;

2-amino-N-[2-(3a-(S)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide;

2-amino-N-[2-(3a-(R,S)-benzyl-2-ethyl-3-oxo-2,3,3a,4,6,7-hexahydro-pyrazolo[4,3-c]pyridin-5-yl)-1 JR)-benzyloxymethyl-2-oxo-ethyl]-isobutyramide;

2-amino-N-[2-(3a-(R)-benzyl-2-ethyl-3-oxo-2,3,3a,4,6,7-hexahydro-pyrazolo[4,3-c]pyridin-5-yl)-1-(R)-benzyloxymethyl-2-oxo-ethyl]-isobutyramide;

2-amino-N-[2-(3a-(S)-benzyl-2-ethyl-3-oxo-2,3,3a,4,6,7-hexahydro-pyrazolo[4,3-c]pyridin-5-yl)-1-(R)-benzyloxymethyl-2-oxo-ethyl]-isobutyramide;

2-amino-N-[2-(3a-(R,S)-benzyl-3-oxo-2-(2,2,2-trifluoro-ethyl)-2,3,3a,4,6,7-hexahydro-pyrazolo[4,3-c]pyridin-5-yl)-1-(R)-benzyloxymethyl-2-oxo-ethyl]-isobutyramide;

2-amino-N-[2-(3a-(R)-benzyl-3-oxo-2-(2,2,2-trifluoro-ethyl)-2,3,3a,4,6,7-hexahydro-pyrazolo[4,3-c]pyridin-5-yl)-1-(R)-benzyloxymethyl-2-oxo-ethyl]-isobutyramide;

2-amino-N-[2-(3a-(S)-benzyl-3-oxo-2-(2,2,2-trifluoro-ethyl)-2,3,3a,4,6,7-hexahydro-pyrazolo[4,3-c]pyridin-5-yl)-1-(R)-benzyloxymethyl-2-oxo-ethyl]-isobutyramide;

2-amino-N-[1-(R)-benzyloxymethyl-2-(3a-(R,S)-(4-fluoro-benzyl)-2-methyl-3-oxo-2,3,3a,4,6,7-hexahydro-pyrazolo[4,3-c]pyridin-5-yl)-2-oxo-ethyl]-isobutyramide;

2-amino-N-[1-(R)-benzyloxymethyl-2-(3a-(R)-(4-fluoro-benzyl)-2-methyl-3-oxo-2,3,3a,4,6,7-hexahydro-pyrazolo[4,3-c]pyridin-5-yl)-2-oxo-ethyl]-isobutyramide;

2-amino-N-[1-(R)-benzyloxymethyl-2-(3a-(S)-(4-fluoro-benzyl)-2-methyl-3-oxo-2,3,3a,4,6,7-hexahydro-pyrazolo[4,3-c]pyridin-5-yl)-2-oxo-ethyl]-isobutyramide;

2-amino-N-[2-(3a-(R,S)-benzyl-2-tert-butyl-3-oxo-2,3,3a,4,6,7-hexahydro-pyrazolo[4,3-c]pyridin-5-yl)-1-(R)-benzyloxymethyl-2-oxo-ethyl]-isobutyramide;

2-amino-N-[2-(3a-(R)-benzyl-2-tert-butyl-3-oxo-2,3,3a,4,6,7-hexahydro-pyrazolo[4,3-c]pyridin-5-yl)-1-(R)-benzyloxymethyl-2-oxo-ethyl]-isobutyramide;

2-amino-N-[2-(3a-(S)-benzyl-2-tert-butyl-3-oxo-2,3,3a,4,6,7-hexahydro-pyrazolo[4,3-c]pyridin-5-yl)-1-(R)-benzyloxymethyl-2-oxo-ethyl]-isobutyramide;

2-amino-N-[2-(3a-(R,S)-benzyl-3-oxo-2,3,3a,4,6,7-hexahydro-pyrazolo[4,3-c]pyridin-5-yl)-1-(R)-benzyloxymethyl-2-oxo-ethyl]-isobutyramide;

2-amino-N-[2-(3a-(R)-benzyl-3-oxo-2,3,3a,4,6,7-hexahydro-pyrazolo[4,3-c]pyridin-5-yl)-1-(R)-benzyloxymethyl-2-oxo-ethyl]-isobutyramide;

2-amino-N-[2-(3a-(S)-benzyl-3-oxo-2,3,3a,4,6,7-hexahydro-pyrazolo[4,3-c]pyridin-5-yl)-1-(R)-benzyloxymethyl-2-oxo-ethyl]-isobutyramide;

2-amino-N-[1-(R)-benzyloxymethyl-2-(2-methyl-3-oxo-3a-(R,S)-pyridin-2-ylmethyl-2,3,3a,4,6,7-hexahydro-pyrazolo[4,3-c]pyridin-5-yl)-2-oxo-ethyl]-2-methyl-propionamide;

2-amino-N-[1-(R)-benzyloxymethyl-2-(2-methyl-3-oxo-3a-(R)-pyridin-2-ylmethyl-2,3,3a,4,6,7-hexahydro-pyrazolo[4,3-c]pyridin-5-yl)-2-oxo-ethyl]-2-methyl-propionamide;

2-amino-N-[1-(R)-benzyloxymethyl-2-(2-methyl-3-oxo-3a-(S)-pyridin-2-ylmethyl-2,3,3a,4,6,7-hexahydro-pyrazolo[4,3-c]pyridin-5-yl)-2-oxo-ethyl]-2-methyl-propionamide;

2-amino-N-[1-(R)-(3-chloro-benzyloxymethyl)-2-oxo-2-(3-oxo-3a-(R,S)-pyridin-2-ylmethyl-2-(2,2,2-trifluoro-ethyl)-2,3,3a,4,6,7-hexahydro-pyrazolo[4,3-c]pyridin-5-yl)-ethyl]-2-methyl-propionamide;

2-amino-N-[1-(R)-(3-chloro-benzyloxymethyl)-2-oxo-2-(3-oxo-3a-(R)-pyridin-2-ylmethyl-2-(2,2,2-trifluoro-ethyl)-2,3,3a,4,6,7-hexahydro-pyrazolo[4,3-c]pyridin-5-yl)-ethyl]-2-methyl-propionamide;

2-amino-N-[1-(R)-(3-chloro-benzyloxymethyl)-2-oxo-2-(3-oxo-3a-(S)-pyridin-2-ylmethyl-2-(2,2,2-trifluoro-ethyl)-2,3,3a,4,6,7-hexahydro-pyrazolo[4,3-c]pyridin-5-yl)-ethyl]-2-methyl-propionamide;

2-amino-N-[1-(R)-(4-chloro-benzyloxymethyl)-2-oxo-2-(3-oxo-3a-(R,S)-pyridin-2-ylmethyl-2-(2,2,2-trifluoro-ethyl)-2,3,3a,4,6,7-hexahydro-pyrazolo[4,3-c]pyridin-5-yl)-ethyl]-2-methyl-propionamide;

2-amino-N-[1-(R)-(4-chloro-benzyloxymethyl)-2-oxo-2-(3-oxo-3a-(R)-pyridin-2-ylmethyl-2-(2,2,2-trifluoro-ethyl)-2,3,3a,4,6,7-hexa hydro-pyrazolo[4,3-c]pyridin-5-yl)-ethyl]-2-methyl-propionamide;

2-amino-N-[1-(R)-(4-chloro-benzyloxymethyl)-2-oxo-2-(3-oxo-3a-(S)-pyridin-2-ylmethyl-2-(2,2,2-trifluoro-ethyl)-2,3,3a,4,6,7-hexahydro-pyrazolo[4,3-c]pyridin-5-yl)-ethyl]-2-methyl-propionamide;

2-amino-N-[1-(R)-(2,4-dichloro-benzyloxymethyl)-2-oxo-2-(3-oxo-3a-(R,S)-pyridin-2-ylmethyl-2-(2,2,2-trifluoro-ethyl)-2,3,3a,4,6,7-hexahydro-pyrazolo[4,3-c]pyridin-5-yl)-ethyl]-2-methyl-propionamide;

2-amino-N-[1-(R)-(2,4-dichloro-benzyloxymethyl)-2-oxo-2-(3-oxo-3a-(R)-pyridin-2-ylmethyl-2-(2,2,2-trifluoro-ethyl)-2,3,3a,4,6,7-hexa hydro-pyrazolo[4,3-c]pyridin-5-yl)-ethyl]-2-methyl-propionamide;

2-amino-N-[1-(R)-(2,4-dichloro-benzyloxymethyl)-2-oxo-2-(3-oxo-3a-(S)-pyridin-2-yl)-ethyl-2-(2,2,2-trifluoro-ethyl)-2,3,3a,4,6,7-hexahydro-pyrazolo[4,3-c]pyridin-5-yl)-ethyl]-2-methyl-propionamide;

2-amino-N-[1-(R)-(4-chloro-thiophen-2-ylmethoxymethyl)-2-oxo-2-(3-oxo-3a-(R,S)-pyridin-2-ylmethyl-2-(2,2,2-trifluoro-ethyl)-2,3,3a,4,5,7-hexahydro-pyrazolo[3,4-c]pyridin-6-yl)-ethyl]-2-methyl-propionamide;

2-amino-N-[1-(R)-(4-chloro-thiophen-2-ylmethoxymethyl)-2-oxo-2-(3-oxo-3a-(R)-pyridin-2-ylmethyl-2-(2,2,2-trifluoro-ethyl)-2,3,3a,4,5,7-hexahydro-pyrazolo[3,4-c]pyridin-6-yl)-ethyl]-2-methyl-propionamide;

2-amino-N-[1-(R)-(4-chloro-thiophen-2-ylmethoxymethyl)-2-oxo-2-(3-oxo-3a-(S)-pyridin-2-ylmethyl-2-(2,2,2-trifluoro-ethyl)-2,3,3a,4,5,7-hexahydro-pyrazolo[3,4-c]pyridin-6-yl)-ethyl]-2-methyl-propionamide;

2-amino-N-[1-(R)-(2,4-difluoro-benzyloxymethyl)-2-oxo-2-(3-oxo-3a-(R,S)-pyridin-2-ylmethyl-2-(2,2,2-trifluoro-ethyl)-2,3,3a,4,6,7-hexahydro-pyrazolo[4,3-c]pyridin-5-yl)-ethyl]-2-methyl-propionamide;

2-amino-N-[1-(R)-(2,4-difluoro-benzyloxymethyl)-2-oxo-2-(3-oxo-3a-(R)-pyridin-2-ylmethyl-2-(2,2,2-trifluoro-ethyl)-2,3,3a,4,6,7-hexa hydro-pyrazolo[4,3-c]pyridin-5-yl)-ethyl]-2-methyl-propionamide;

2-amino-N-[1-(R)-(2,4-difluoro-benzyloxymethyl)-2-oxo-2-(3-oxo-3a-(S)-pyridin-2-ylmethyl-2-(2,2,2-trifluoro-ethyl)-2,3,3a,4,6,7-hexahydro-pyrazolo[4,3-c]pyridin-5-yl)-ethyl]-2-methyl-propionamide;

2-amino-N-[2-(3a-(R,S)-benzyl-2-methyl-3-oxo-2,3,3a,4,6,7-hexahydro-pyrazolo[4,3-c]pyridin-5-yl)-1-(R)-(3,4-difluoro-benzyloxymethyl)-2-oxo-ethyl]-2-methyl-propionamide;

2-amino-N-[2-(3a-(R)-benzyl-2-methyl-3-oxo-2,3,3a,4,6,7-hexahydro-pyrazolo[4,3-c]pyridin-5-yl)-1-(R)-(3,4-difluoro-benzyloxymethyl)-2-oxo-ethyl]-2-methyl-propionamide; and 2-amino-N-[2-(3a-(S)-benzyl-2-methyl-3-oxo-2,3,3a,4,6,7-hexahydro-pyrazolo[4,3-c]pyridin-5-yl)-1-(R)-(3,4-difluoro-benzyloxymethyl)-2-oxo-ethyl]-2-methyl-propionamide;

or a pharmaceutically acceptable salt thereof;

[4] The use according to or [2], wherein the compound is selected from the group consisting of the following compounds:

2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide; and 2-amino-N-[1-(R)-(2,4-difluoro-benzyloxymethyl)-2-oxo-2-(3-oxo-3a-(R)-pyridin-2-ylmethyl-2-(2,2,2-trifluoro-ethyl)-2,3,3a,4,6,7-hexahydro-pyrazolo[4,3-c]pyridin-5-yl)-ethyl]-2-methyl-propionamide;

or is a pharmaceutically acceptable salt thereof;

[5] The use according to any one of to [1] [4], wherein the cachexia is cancer cachexia, tuberculous cachexia, diabetic cachexia, hemodyscrasia-associated related cachexia, endocrine disease-associated cachexia, chronic obstructive pulmonary disease-associated cachexia, chronic kidney disease-associated cachexia, cardiac failure-associated cachexia, infectious disease-associated cachexia, or acquired immunodeficiency syndrome-associated cachexia;

[6] A use of a compound according to any one of [1] to [4] or a pharmaceutically acceptable salt thereof in combination with one or more second active agents;

[7] The use according to [6], wherein the second active agents are any of a chemotherapeutic agent, an immunotherapeutic agent, a drug which is documented as having an ameliorating effect on cachexia in an animal model or clinical practice, and a diuretic agent;

[8] A method for the treatment of cachexia, which comprises administering to a human or an animal an effective amount of a compound according to any one of [1] to [4] or a pharmaceutically acceptable salt thereof;

[9] A pharmaceutical composition for the treatment of cachexia, comprising a compound according to any one of [1] to [4] or a pharmaceutically acceptable salt thereof;

[10] A kit for the treatment of cachexia, comprising a compound according to any one of [1] to [4] or a pharmaceutically acceptable salt thereof;

[11] The kit according to [10], which comprises a compound according to any one of [1] to [4] or a pharmaceutically acceptable salt thereof, one or more kinds of second active agents, and a container; and

[12] A commercial package comprising a pharmaceutical composition containing a compound according to any one of [1] to [4] or a pharmaceutically acceptable salt thereof and a written matter associated with said pharmaceutical composition, the written matter stating that said pharmaceutical composition can or should be used for treating cachexia.

Advantageous Effect of Invention

The therapeutic agent of the present invention is used as an agent for treatment of cachexia which develops in chronic diseases such as malignant tumor, tuberculosis, diabetes, hemodyscrasia, endocrine disease, chronic obstructive pulmonary disease, chronic kidney disease, cardiac failure, infectious disease, and acquired immunodeficiency syndrome. The therapeutic agent of the present invention is conducive to relief of the systemic syndrome with cardinal symptoms such as progressive loss of body weight (inclusive of weight loss due to lipolysis and weight loss due to myolysis), anemia, edema, and anorexia, in said chronic diseases.

Since transplantation of cancer cells or cancer tissue in animals causes decrease in food consumption and in body weight, these animals have been used as an animal model of cachexia ("Endocrinology", Volume 148, 3004-3012, 2007). The inventors of the present invention searched to find out a compound group effective for the disease model and finally discovered that a compound of the general formula (I) was effective for the treatment of symptoms of cachexia. A compound of the general formula (I) is disclosed as a substance for increasing growth hormone secretion in WO97/024369. This patent literature describes various use applications which are useful for osteoporosis, congestive heart failure, frailty associated with aging, obesity; accelerating bone fracture repair, attenuating protein catabolic response after a major operation, reducing cachexia and protein loss due to chronic illness, accelerating wound healing, or accelerating the recovery of burn patients or patients having undergone major surgery; improving muscle strength, mobility, maintenance of skin thickness, metabolic homeostasis, or renal homeostasis; and growth of children with growth hormone deficiency. However, in the experiments there, growth hormone secretion was merely measured in cultured pituitary cells in rats as the effect of promoting growth hormone secretion, and experimental data, which shows the compound of the present invention is effective for cachexia, have never been described. Furthermore, in other known literature information, there is no scientific evidence that a compound of general formula (I) is effective in the treatment of cachexia.

Thus, for the first time ever, the present invention has disclosed that a compound of the general formula (I) is effective for the treatment of the symptoms of cachexia.

DESCRIPTION OF EMBODIMENTS

The compounds represented by the following formula (I) and a pharmaceutically acceptable salt thereof, wherein the compounds are disclosed in WO97/024369, include solvates, complexes, polymorphs, prodrugs, isomers, and isotopically labeled compounds thereof.

That is, the present invention relates to a compound represented by the following formula (I):

(I)

{Chem. 5}

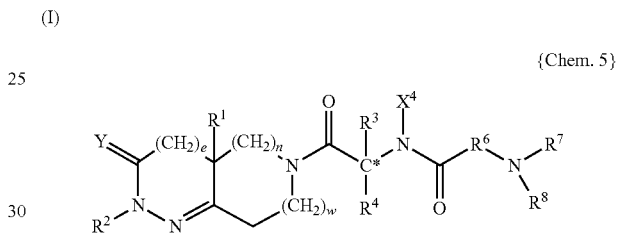

wherein
e is 0 or 1;
n and w are each independently 0, 1 or 2, provided that w and n cannot both be 0 at the same time;
Y is oxygen or sulfur;
$R^1$ is hydrogen, —CN, —$(CH_2)_q N(X^6)C(O)X^6$, —$(CH_2)_q N(X^6)C(O)(CH_2)_t$-$A^1$, —$(CH_2)_q N(X^6)SO_2(CH_2)_t$-$A^1$, —$(CH_2)_q N(X^6)SO_2 X^6$, —$(CH_2)_q N(X^6)C(O)N(X^6)(CH_2)_t$-$A^1$, —$(CH_2)_q N(X^6)C(O)N(X^6)(X^6)$, —$(CH_2)_q C(O)N(X^6)(X^6)$, —$(CH_2)_q C(O)N(X^6)(CH_2)_t$-$A^1$, —$(CH_2)_q C(O)OX^6$, —$(CH_2)_q C(O)O(CH_2)_t$-$A^1$, —$(CH_2)_q OX^6$, —$(CH_2)_q OC(O)X^6$, —$(CH_2)_q OC(O)(CH_2)_t$-$A^1$, —$(CH_2)_q OC(O)N(X^6)$ $(CH_2)_t$-$A^1$, —$(CH_2)_q OC(O)N(X^6)C(O)OX^6$, —$(CH_2)_q C(O)X^6$, —$(CH_2)_q C(O)(CH_2)_t$-$A^1$, —$(CH_2)_q N(X^6)C(O)OX^6$, —$(CH_2)_q N(X^6)SO_2 N(X^6)(X^6)$, —$(CH_2)_q S(O)_m X^6$, —$(CH_2)_q S(O)_m (CH_2)_t$-$A^1$, —$(C_1$-$C_{10})$alkyl, —$(CH_2)_t$-$A^1$, —$(CH_2)_q$—$(C_3$-$C_7)$cycloalkyl, —$(CH_2)_q$—$Y^1$—$(C_1$-$C_5)$alkyl, —$(CH_2)_q$—$Y^1$—$(CH_2)_t$- $A^1$ or —$(CH_2)_q$—$Y^1$— $(CH_2)_t$—$(C_3$-$C_7)$cycloalkyl
(where the alkyl and cycloalkyl groups in the definition of $R^1$ are optionally substituted with $(C_1$-$C_4)$alkyl, hydroxyl, $(C_1$-$C_4)$alkoxy, carboxyl, —$CONH_2$, —$S(O)_m(C_1$-$C_6)$alkyl, —$CO_2(C_1$-$C_4)$alkyl ester, 1H-tetrazol-5-yl or 1, 2 or 3 fluoro;
$Y^1$ is O, $S(O)_m$, —$C(O)NX^6$—, —CH=CH—, —C≡C—, —$N(X^6)C(O)$—, —$C(O)NX^6$—, —$CO(O)O$—, —$OC(O)N$ $(X^6)$— or —$OC(O)$—;
q is 0, 1, 2, 3 or 4;
t is 0, 1, 2 or 3;
said $(CH_2)_q$ group and $(CH_2)_t$ group may each be optionally substituted with hydroxyl, $(C_1$-$C_4)$alkoxy, carboxyl, —$CONH_2$, —$S(O)_m(C_1$-$C_6)$alkyl, —$CO_2(C_1$-$C_4)$alkyl ester, 1H-tetrazol-5-yl, 1, 2 or 3 fluoro, or 1 or 2 $(C_1$-$C_4)$alkyl);
$R^2$ is hydrogen, $(C_1$-$C_8)$alkyl, —$(C_0$-$C_3)$alkyl-$(C_3$-$C_8)$cycloalkyl, —$(C_1$-$C_4)$alkyl-$A^1$ or $A^1$ (where the alkyl groups and cycloalkyl groups in the definition of $R^2$ are optionally substituted with hydroxyl, —C(O)OX$^6$, —C(O)N(X$^6$)(X$^6$), —N(X$^6$)(X$^6$), —S(O)$_m$(C$_1$-C$_6$)alkyl, —C(O)A$^1$, —C(O)(X$^6$), CF$_3$, CN or 1, 2 or 3 halogen);

$R^3$ is A$^1$, (C$_1$-C$_{10}$)alkyl, —(C$_1$-C$_6$)alkyl-A$^1$, —(C$_1$-C$_6$)alkyl-(C$_3$-C$_7$)cycloalkyl, C$_5$)alkyl-X$^1$—(C$_1$-C$_5$)alkyl, —(C$_0$-C$_5$)alkyl-X$^1$—(C$_0$-C$_5$)alkyl-A$^1$ or —(C$_1$-C$_5$)alkyl-X$^1$—(C$_1$-C$_5$)alkyl-(C$_3$-C$_7$)cycloalkyl (where the alkyl groups in the definition of $R^3$ are optionally substituted with —S(O)$_m$(C$_1$-C$_6$)alkyl, —C(O)OX$^3$, 1, 2, 3, 4 or 5 halogen, or 1, 2 or 3 OX$^3$;

$X^1$ is O, S(O)$_m$, —N(X$^2$)C(O)—, —C(O)N(X$^2$)—, —OC(O)—, —C(O)O—, —CX$^2$=CX$^2$—, —N(X$^2$)C(O)O—, —OC(O)N(X$^2$)— or —C≡C—);

$R^4$ is hydrogen, (C$_1$-C$_6$)alkyl or (C$_3$-C$_7$)cycloalkyl, or $R^4$ is taken together with $R^3$ and the carbon atom to which they are attached and form (C$_5$-C$_7$)cycloalkyl, (C$_5$-C$_7$)cycloalkenyl, a partially saturated or fully saturated 4- to 8-membered ring having 1 to 4 heteroatoms independently selected from the group consisting of oxygen, sulfur and nitrogen, or is a bicyclic ring system consisting of a partially saturated or fully saturated 5- or 6-membered ring, fused to a partially saturated, fully unsaturated or fully saturated 5- or 6-membered ring, optionally having 1 to 4 heteroatoms independently selected from the group consisting of nitrogen, sulfur and oxygen;

$X^4$ is hydrogen or (C$_1$-C$_6$)alkyl or $X^4$ is taken together with $R^4$ and the nitrogen atom to which $X^4$ is attached and the carbon atom to which $R^4$ is attached and form a five to seven membered ring;

$R^6$ is a bond or is

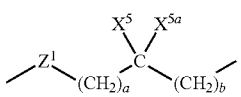

{Chem. 6}

(where a and b are independently 0, 1, 2 or 3;

$X^5$ and $X^{5a}$ are each independently selected from the group consisting of hydrogen, trifluoromethyl, A$^1$ and optionally substituted (C$_1$-C$_6$)alkyl; the optionally substituted (C$_1$-C$_6$)alkyl in the definition of $X^5$ and $X^{5a}$ is optionally substituted with a substituent selected from the group consisting of A$^1$, OX$^2$, —S(O)$_m$(C$_1$-C$_6$)alkyl, —C(O)OX$^2$, (C$_3$-C$_7$)cycloalkyl, —N(X$^2$)(X$^2$) and —C(O)N(X$^2$)(X$^2$); or the carbon bearing $X^5$ or $X^{5a}$ forms one or two alkylene bridges with the nitrogen atom bearing $R^7$ and $R^8$ wherein each alkylene bridge contains 1 to 5 carbon atoms, provided that when one alkylene bridge is formed then $X^5$ or $X^{5a}$ but not both may be on the carbon atom and $R^7$ or $R^8$ but not both may be on the nitrogen atom and further provided that when two alkylene bridges are formed then $X^5$ and $X^{5a}$ cannot be on the carbon atom and $R^7$ and $R^8$ cannot be on the nitrogen atom; or $X^5$ is taken together with $X^{5a}$ and the carbon atom to which they are attached and form a partially saturated or fully saturated 3- to 7-membered ring, or a partially saturated or fully saturated 4- to 8-membered ring having 1 to 4 heteroatoms independently selected from the group consisting of oxygen, sulfur and nitrogen, or $X^5$ is taken together with $X^{5a}$ and the carbon atom to which they are attached and form a bicyclic ring system consisting of a partially saturated or fully saturated 5- or 6-membered ring, optionally having 1 or 2 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;

$Z^1$ is a single bond, O or N—X$^2$, provided that when a and b are both 0 then $Z^1$ is not N—X$^2$ or O);

$R^7$ and $R^8$ are independently hydrogen or optionally substituted (C$_1$-C$_6$)alkyl (where the optionally substituted (C$_1$-C$_6$)alkyl in the definition of $R^7$ and $R^8$ is optionally independently substituted with A$^1$, —C(O)O—(C$_1$-C$_6$)alkyl, —S(O)$_m$(C$_1$-C$_6$)alkyl, 1 to 5 halogen, 1 to 3 hydroxy, 1 to 3 —O—C(O)(C$_1$-C$_{10}$)alkyl or 1 to 3 (C$_1$-C$_6$)alkoxy); or $R^7$ and $R^8$ can be taken together to form —(CH$_2$)$_r$-L-(CH$_2$)$_r$—; where L is C(X$^2$)(X$^2$), S(O)$_m$ or N(X$^2$);

A$^1$ for each occurrence is independently (C$_5$-C$_7$)cycloalkenyl, phenyl or a partially saturated, fully saturated or fully unsaturated 4- to 8-membered ring optionally having 1 to 4 heteroatoms independently selected from the group consisting of oxygen, sulfur and nitrogen, a bicyclic ring system consisting of a partially saturated, fully unsaturated or fully saturated 5- or 6-membered ring, optionally having 1 to 4 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen; A$^1$ for each occurrence is independently optionally substituted, in one or optionally both rings if A$^1$ is a bicyclic ring system, with up to three substituents, each substituent independently selected from the group consisting of F, Cl, Br, I, OCF$_3$, OCF$_2$H, CF$_3$, CH$_3$, OCH$_3$, —OX$^6$, —C(O)N(X$^6$)(X$^6$), —C(O)OX$^6$, oxo, (C$_1$-C$_6$)alkyl, nitro, cyano, benzyl, —S(O)$_m$(C$_1$-C$_6$)alkyl, 1H-tetrazol-5-yl, phenyl, phenoxy, phenylalkyloxy, halophenyl, methylenedioxy, —N(X$^6$)(X$^6$), —N(X$^6$)C(O)(X$^6$), —SO$_2$N(X$^6$)(X$^6$), —N(X$^6$)SO$_2$-phenyl, —N(X$^6$)SO$_2$X$^6$, —CONX$^{11}$X$^{12}$, —SO$_2$NX$^{11}$X$^{12}$, —NX$^6$SO$_2$X$^{12}$, —NX$^6$CONX$^{11}$X$^{12}$, —NX$^6$SO$_2$NX$^{11}$X$^{12}$, —NX$^6$C(O)X$^{12}$, imidazolyl, thiazolyl and tetrazolyl, provided that if A$^1$ is optionally substituted with methylenedioxy then it can only be substituted with one methylenedioxy (where X$^{11}$ is hydrogen or optionally substituted (C$_1$-C$_6$) alkyl; the optionally substituted (C$_1$-C$_6$)alkyl defined for X$^{11}$ is optionally independently substituted with phenyl, phenoxy, (C$_1$-C$_6$)alkoxycarbonyl, —S(O)$_m$(C$_1$-C$_6$)alkyl, 1 to 5 halogen, 1 to 3 hydroxy, 1 to 3 (C$_1$-C$_{10}$)alkanoyloxy or 1 to 3 (C$_1$-C$_6$)alkoxy; X$^{12}$ is hydrogen, (C$_1$-C$_6$)alkyl, phenyl, thiazolyl, imidazolyl, furyl or thienyl, provided that when X$^{12}$ is not hydrogen, X$^{12}$ is optionally substituted with one to three substituents independently selected from the group consisting of Cl, F, CH$_3$, OCH$_3$, OCF$_3$ and CF$_3$;

or X$^{11}$ and X$^{12}$ are taken together to form —(CH$_2$)$_r$-L$^1$-(CH$_2$)$_r$—;

where L$^1$ is C(X$^2$)(X$^2$), O, S(O)$_m$ or N(X$^2$)); r for each occurrence is independently 1, 2 or 3;

$X^2$ for each occurrence is independently hydrogen, optionally substituted (C$_1$-C$_6$)alkyl, or optionally substituted (C$_3$-C$_7$)cycloalkyl, where the optionally substituted (C$_1$-C$_6$) alkyl and optionally substituted (C$_3$-C$_7$)cycloalkyl in the definition of $X^2$ are optionally independently substituted with —S(O)$_m$(C$_1$-C$_6$)alkyl, —C(O)OX$^3$, 1 to 5 halogen or 1 to 3 OX$^3$;

$X^3$ for each occurrence is independently hydrogen or (C$_1$-C$_6$)alkyl;

$X^6$ is independently hydrogen, optionally substituted (C$_1$-C$_6$)alkyl, (C$_2$-C$_6$)halogenated alkyl, optionally substituted (C$_3$-C$_7$)cycloalkyl, (C$_3$-C$_7$)-halogenated cycloalkyl, where optionally substituted (C$_1$-C$_6$)alkyl and optionally substituted (C$_3$-C$_7$)cycloalkyl in the definition of X$^6$ is optionally independently substituted with 1 or 2 (C$_1$-C$_4$)alkyl, hydroxyl, (C$_1$-C$_4$)alkoxy, carboxyl, CONH$_2$, —S(O)$_m$(C$_1$-C$_6$)alkyl, carboxylate, (C$_1$-C$_4$)alkyl ester, or 1H-tetrazol-5-yl; or when there are two X$^6$ groups on one atom and both X$^6$ are independently (C$_1$-C$_6$)alkyl, the two (C$_1$-C$_6$)alkyl groups may be optionally joined and, together with the atom to which the two X$^6$ groups are attached, form a 4- to 9-membered ring optionally having oxygen, sulfur or NX$^7$; X$^7$ is hydrogen or (C$_1$-C$_6$)alkyl optionally substituted with hydroxyl; and m for each occurrence is independently 0, 1 or 2; with the proviso that:

X$^6$ and X$^{12}$ cannot be hydrogen when it is attached to C(O) or SO$_2$ in the form C(O)X$^6$, C(O)X$^{12}$, SO$_2$X$^6$ or SO$_2$X$^{12}$; and when R$^6$ is a bond then L is N(X$^2$) and each r in the definition —(CH$_2$)$_r$-L-(CH$_2$)$_r$— is independently 2 or 3.

A preferred group of compounds, designated the "A Group", contains those compounds having the formula (I) as shown hereinabove wherein X$^4$ is hydrogen; R$^4$ is hydrogen or methyl; R$^7$ is hydrogen or (C$_1$-C$_3$)alkyl; R$^8$ is hydrogen or (C$_1$-C$_3$)alkyl optionally substituted with one or two hydroxyl groups;

R$^6$ is

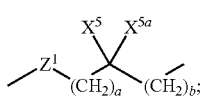

{Chem. 7} where Z$^1$ is a single bond and a is 0 or 1;

X$^5$ and X$^{5a}$ are each independently hydrogen, trifluoromethyl, phenyl, optionally substituted (C$_1$-C$_6$)alkyl; where the optionally substituted (C$_1$-C$_6$)alkyl is optionally substituted with OX$^2$, imidazolyl, phenyl, indolyl, p-hydroxyphenyl, (C$_5$-C$_7$)cycloalkyl, —S(O)$_m$(C$_1$-C$_6$)alkyl, —N(X$^2$)(X$^2$) or —C(O)N(X$^2$)(X$^2$);

or X$^5$ and R$^7$ are taken together to form a (C$_1$-C$_5$)alkylene bridge, and the other substituents not defined for the "A Group" compounds are as defined for the formula (I) hereinabove.

A group of compounds, which is preferred among the "A Group" of compounds, designated the "B Group", contains those compounds of the "A Group", having the formula (I) as shown hereinabove, wherein b is 0; X$^5$ and X$^{5a}$ are each independently hydrogen, (C$_1$-C$_3$)alkyl or hydroxy(C$_1$-C$_3$)alkyl; R$^3$ is selected from the group consisting of 1-indolyl-CH$_2$—, 2-indolyl-CH$_2$—, 1-naphthyl-CH$_2$—, 2-naphthyl-CH$_2$—, 1-benzimidazolyl-CH$_2$—, 2-benzimidazolyl-CH$_2$—, phenyl-(C$_1$-C$_4$)alkyl-, 2-pyridyl-(C$_1$-C$_4$)alkyl-, 3-pyridyl-(C$_1$-C$_4$)alkyl-, 4-pyridyl-(C$_1$-C$_4$)alkyl-, phenyl-CH$_2$—SCH$_2$—, thienyl-(C$_1$-C$_4$)alkyl-, phenyl-(C$_0$-C$_3$)alkyl-O—CH$_2$—, phenyl-CH$_2$—O-phenyl-CH$_2$—, and 3-benzothienyl-CH$_2$—; where the aryl portion(s) of the groups defined for R$^3$ are optionally substituted with one to three substituents, each substituent being independently selected from the group consisting of methylenedioxy, F, Cl, CH$_3$, OCH$_3$, OCF$_3$, OCF$_2$H and CF$_3$.

A group of compounds, which is preferred among the "B Group" of compounds, designated the "C Group", contain those compounds of the "B Group", having the formula (I) as shown hereinabove, wherein R$^4$ is hydrogen; a is 0; n is 1 or 2; w is 0 or 1; X$^5$ and X$^{5a}$ are each independently, hydrogen, methyl or hydroxymethyl, provided that when X$^5$ is hydrogen then X$^{5a}$ is not hydrogen; R$^7$ and R$^8$ are each hydrogen; and R$^3$ is phenyl-CH$_2$—O—CH$_2$—, phenyl-CH$_2$—S—CH$_2$—, 1-naphthyl-CH$_2$—, 2-naphthyl-CH$_2$—, phenyl-(CH$_2$)$_3$— or 3-indolyl-CH$_2$—; where the aryl portion of the groups defined for R$^3$ is optionally substituted with one to three substituents, each substituent being independently selected from the group consisting of fluoro, chloro, methyl, OCH$_3$, OCF$_2$H, OCF$_3$ and CF$_3$.

A group of compounds, which is preferred among the "C Group" of compounds, designated the "D Group", contains those compounds of the "C Group", having the formula (I) as shown hereinabove, wherein R$^1$ is —(CH$_2$)$_r$-A$^1$, —(CH$_2$)$_q$—(C$_3$-C$_7$)cycloalkyl or (C$_1$-C$_{10}$)alkyl; where A$^1$ in the definition of R$^1$ is optionally substituted with one to three substituents, each substituent being independently selected from the group consisting of fluoro, chloro, methyl, OCH$_3$, OCF$_2$H, OCF$_3$ and CF$_3$; the cycloalkyl and alkyl groups in the definition of R$^1$ are optionally substituted with (C$_1$-C$_4$)alkyl, hydroxyl, (C$_1$-C$_4$)alkoxy, carboxyl, CONH$_2$, —S(O)$_m$(C$_1$-C$_6$)alkyl, —CO$_2$(C$_1$-C$_4$)alkyl ester, 1H-tetrazol-5-yl or 1 to 3 fluoro; Y is O; R$^2$ is hydrogen, —(C$_0$-C$_3$) alkyl-(C$_3$-C$_8$)cycloalkyl, phenyl or (C$_1$-C$_8$)alkyl where the (C$_1$-C$_8$)alkyl group is optionally substituted with hydroxyl, —CF$_3$ or 1 to 3 halogen.

A group of compounds, which is preferred among the "D Group" of compounds, designated the "E Group", contains those compounds of the "D Group" wherein w is 0 and n is 1.

Another group of compounds, which is preferred among the "D Group" of compounds, designated the "F Group", are those compounds of the "D Group", having the formula (I) as shown hereinabove, wherein e is 0; n and w are each 1; R$^1$ is —(CH$_2$)$_t$-A$^1$; where A$^1$ in the definition of R$^1$ is phenyl, thienyl, thiazolyl, pyridyl or pyrimidyl which is optionally substituted with one to three substituents, each substituent being independently selected from the group consisting of F, Cl, Me, OMe, CF$_3$, OCF$_3$ and OCF$_2$H; t is 0, 1 or 2; and R$^3$ is phenyl-CH$_2$—O—CH$_2$—, phenyl-(CH$_2$)$_3$— or 3-indolyl-CH$_2$—, where the aryl portion is optionally substituted with one to three substituents, each substituent being independently selected from the group consisting of F, Cl, Me, OMe, CF$_3$, OCF$_3$ or OCF$_2$H.

A group of compounds, which is preferred among the "F Group" of compounds, designated the "G Group", contains those compounds of the "F Group", having the formula (I) as shown hereinabove, wherein X$^5$ and X$^{5a}$ are each methyl; R$^1$ is —CH$_2$-phenyl, —CH$_2$-4-fluoro-phenyl, —CH$_2$-pyridyl or —CH$_2$-thiazolyl and R$^2$ is hydrogen, methyl, ethyl, t-butyl or —CH$_2$CF$_3$.

A group of compounds, which is preferred among the "G Group" of compounds, designated the "G$^1$ Group", contains those compounds of the "G Group", and have the formula:

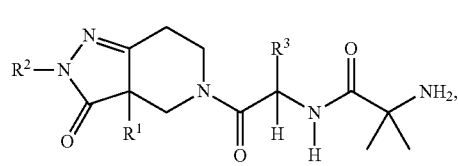

{Chem. 8} the racemic-diastereomeric mixtures and optical isomers of said compounds
wherein
R$^1$ is —CH$_2$-phenyl, R$^2$ is methyl and R$^3$ is —(CH$_2$)$_3$-phenyl;

R¹ is —CH₂-phenyl, R² is methyl and R³ is 3-indolyl-CH₂—;

R¹ is —CH₂-phenyl, R² is ethyl and R³ is 3-indolyl-CH₂—;

R¹ is —CH₂-4-fluoro-phenyl, R² is methyl and R³ is 3-indolyl-CH₂—;

R¹ is —CH₂-phenyl, R² is methyl and R³ is —CH₂—O—CH₂-phenyl;

R¹ is —CH₂-phenyl, R² is ethyl and R³ is —CH₂—O—CH₂-phenyl;

R¹ is —CH₂-phenyl, R² is —CH₂—CF₃ and R³ is —CH₂—O—CH₂-phenyl;

R¹ is —CH₂-4-fluoro-phenyl, R² is methyl and R³ is —CH₂—O—CH₂-phenyl;

R¹ is —CH₂-phenyl, R² is t-butyl and R³ is —CH₂—O—CH₂-phenyl; or

R¹ is —CH₂-phenyl, R² is methyl and R³ is —CH₂—O—CH₂-3,4-di-fluoro-phenyl.

The diastereomeric mixture of 2-amino-N-[2-(3a-(R,S)-benzyl-2-methyl-3-oxo-2,3,3a,4,6,7-hexahydro-pyrazolo[4,3-c]pyridin-5-yl)-1-(R)-(3,4-difluoro-benzyl-oxymethyl)-2-oxo-ethyl]-2-methyl-propionamide is preferred among the "G¹ Group" of compounds and the separated 3a-(R) and 3a-(S) isomers are preferred of the diastereomeric mixture.

A group of compounds, which is preferred among the "G Group", designated the "H Group", contains those compounds of the "G Group", having the formula (I) as shown hereinabove, wherein R¹ is —CH₂-phenyl and R³ is phenyl-(CH₂)₃—.

The diastereomeric mixture of 2-amino-N-[1-(3a-(R,S)-benzyl-2-methyl-3-oxo-2,3,3a,4,6,7-hexahydro-pyrazolo[4,3-c]pyridine-5-carbonyl)-4-phenyl-(R)-butyl]-isobutyramide is preferred among the "H Group" of compounds and the separated 3a-(R) and 3a-(S) isomers are preferred of the diastereomeric mixture.

A group of compounds, which is preferred among the "G Group", designated the "I Group", contains those compounds of the "G Group" wherein R¹ is —CH₂-phenyl or —CH₂-4-fluoro-phenyl and R³ is 3-indolyl-CH₂—.

The diastereomeric mixture of 2-amino-N-[2-(3a-(R,S)-benzyl-2-methyl-3-oxo-2,3,3a,4,6,7-hexahydro-pyrazolo-[4,3-c]pyridin-5-yl)-1-(R)-(1H-indol-3-ylmethyl)-2-oxo-ethyl]-isobutyramide is preferred among the "I Group" of compounds and the separated 3a-(R) and 3a-(S) isomers are preferred of the diastereomeric mixture.

The diastereomeric mixture of 2-amino-N-[2-(3a-(R,S)-benzyl-2-ethyl-3-oxo-2,3,3a,4,6,7-hexahydro-pyrazolo[4,3-c]pyridin-5-yl)-1-(R)-(1H-indol-3-ylmethyl)-2-oxo-ethyl] isobutyramide is also preferred among the "1 Group" of compounds and the separated 3a-(R) and 3a-(S) isomers are preferred of the diastereomeric mixture.

The diastereomeric mixture of 2-amino-N-[2-[3a-(R,S)-(4-fluoro-benzyl)-2-methyl-3-oxo-2,3,3a,4,6,7-hexahydro-pyrazolo[4,3-c]pyridin-5-yl]-1-(R)-(1H-indol-3-ylmethyl)-2-oxo-ethyl]isobutyramide is also preferred among the "I Group" of compounds and the separated 3a-(R) and 3a-(S) isomers are preferred of the diastereomeric mixture.

A group of compounds which is preferred among the "G Group", designated the "J Group", contains those compounds of the "G Group" wherein R¹ is —CH₂-phenyl or —CH₂-4-fluoro-phenyl and R³ is phenyl-CH₂—O—CH₂—.

The diastereomeric mixture of 2-amino-N-[2-(3a-(R,S)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide is preferred among the "J Group" of compounds, the separated 3a-(R) and 3a-(S) isomers are preferred of the diastereomeric mixture, the 3a-(R) isomer is preferred over the 3a-(S) isomer, and the L-tartaric acid salt of the 3a-(R) isomer is a preferred salt.

The diastereomeric mixture of 2-amino-N-[2-(3a-(R,S)-benzyl-2-ethyl-3-oxo-2,3,3a,4,6,7-hexahydro-pyrazolo[4,3-c]pyridin-5-yl)-1-(R)-benzyloxymethyl-2-oxo-ethyl]-isobutyramide is also preferred among the "J Group" of compounds and the separated 3a-(R) and 3a-(S) isomers are preferred of the diastereomeric mixture.

The diastereomeric mixture of 2-amino-N-{2-[3a-(R,S)-benzyl-3-oxo-2-(2,2,2-trifluoro-ethyl)-2,3,3a,4,6,7-hexahydro-pyrazolo[4,3-c]pyridin-5-yl]-1-(R)-benzyloxymethyl-2-oxo-ethyl}-isobutyramide is also preferred among the "J Group" of compounds, the separated 3a-(R) and 3a-(S) isomers are preferred of the diastereomeric mixture and the 3a-(R) isomer is preferred over the 3a-(S) isomer.

The diastereomeric mixture of 2-amino-N-{1-(R)-benzyloxymethyl-2-[3a-(R,S)-(4-fluoro-benzyl)-2-methyl-3-oxo-2,3,3a,4,6,7-hexahydro-pyrazolo[4,3-c]pyridin-5-yl]-2-oxo-ethyl}-isobutyramide is also preferred among the "J Group" of compounds and the separated 3a-(R) and 3a-(S) isomers are preferred of the diastereomeric mixture.

The diastereomeric mixture of 2-amino-N-[2-(3a-(R,S)-benzyl-2-tert-butyl-3-oxo-2,3,3a,4,6,7-hexahydro-pyrazolo[4,3-c]pyridin-5-yl)-1-(R)-benzyloxymethyl-2-oxo-ethyl]-isobutyramide is also preferred among the "J Group" of compounds and the separated 3a-(R) and 3a-(S) isomers are preferred of the diastereomeric mixture. A group of compounds which is preferred among the "D Group" of compounds, designated the "K Group", contains those compounds of the "D Group" wherein e is 1; n is 1; w is 1; R¹ is —(CH₂)ₜ-A¹; where A¹ in the definition of R¹ is phenyl, thienyl, thiazolyl, pyridyl or pyrimidyl which is optionally substituted with one to three substituents, each substituent being independently selected from the group consisting of F, Cl, Me, OMe, CF₃, OCF₃ and OCF₂H; t is 0, 1 or 2; and R³ is phenyl-CH₂—O—CH₂—, phenyl-(CH₂)₃— or 3-indolyl-CH₂—, where the aryl portion is optionally substituted with one to three substituents, each substituent being independently selected from the group consisting of F, Cl, Me, OMe, CF₃, OCF₃ or OCF₂H.

A group of compounds which is preferred among the "K Group" of compounds, designated the "L Group", are those compounds of the "K Group" wherein X⁵ and X⁵ᵃ are each methyl; R¹ is —CH₂-phenyl, —CH₂-4-fluoro-phenyl, —CH₂-pyridyl or —CH₂-thiazolyl and R² is hydrogen, methyl, ethyl, t-butyl or —CH₂CF₃.

A group of compounds which is preferred among the "L Group", designated the "L¹ Group", are those compounds of the "L Group" wherein R¹ is —CH₂-phenyl; R² is hydrogen or methyl and R³ is —CH₂—O—CH₂-phenyl.

The diastereomeric mixture of 2-amino-N-[2-(3a-(R,S)-benzyl-3-oxo-2,3,3a,4,6,7-hexahydro-pyrazolo[4,3-c]pyridin-5-yl)-1-(R)-benzyloxymethyl-2-oxo-ethyl]-isobutyramide is preferred among the "J Group", the separated 3a-(R) and 3a-(S) isomers are preferred of the diastereomeric mixture and the 3a-(R) isomer is preferred over the 3a-(S) isomer.

Another group of compounds, which is preferred among the "A Group" of compounds, designated the "M Group", contains those compounds of the "A Group", having the formula (I) as shown hereinabove, wherein b is 0; X⁵ and X' a are each independently hydrogen, (C₁-C₃)alkyl or hydroxy (C₁-C₃)alkyl; R³ is selected from the group consisting of 1-indolyl-CH₂—, 2-indolyl-CH₂—, 3-indolyl-CH₂—, 1-naphthyl-$CH_2$—, 2-naphthyl-$CH_2$—, 1-benzimidazolyl-$CH_2$—, 2-benzimidazolyl-$CH_2$—, phenyl-$(C_1$-$C_4)$alkyl-, 2-pyridyl-$(C_1$-$C_4)$alkyl-, 3-pyridyl-$(C_1$-$C_4)$alkyl-, 4-pyridyl-$(C_1$-$C_4)$alkyl-, phenyl-$CH_2$—S—C thienyl-$(C_1$-$C_4)$alkyl-, phenyl-$(C_0$-$C_3)$alkyl-O—$CH_2$—, phenyl-$CH_2$—O-phenyl-$CH_2$—, 3-benzothienyl-$CH_2$—, thienyl-$CH_2$—O—$CH_2$—, thiazolyl-$CH_2$—O—$CH_2$—, pyridyl-$CH_2$—O—$CH_2$—, pyrimidyl-$CH_2$—O—$CH_2$— and phenyl-O—$CH_2$—$CH_2$; where the aryl portion(s) of the groups defined for $R^3$ are optionally substituted with one to three substituents, each substituent being independently selected from the group consisting of methylenedioxy, F, Cl, $CH_3$, $OCH_3$, $OCF_3$, $OCF_2H$ and $CF_3$.

A group of compounds, which is preferred among the "M Group" of compounds, designated the "$M^1$ Group", contains those compounds of the "M Group", having the formula (I) as shown hereinabove, wherein $R^4$ is hydrogen; a is 0; n is 1; w is 1; e is 0; $X^5$ and $X^{5a}$ are each independently, hydrogen, methyl or hydroxymethyl, provided that when $X^5$ is hydrogen then $X^{5a}$ is not hydrogen; $R^1$ and $R^8$ are each hydrogen; Y is oxygen; $R^2$ is hydrogen, methyl, ethyl, propyl, i-propyl, t—butyl, —$CH_2CF_3$, $CF_3$ or —$CH_2$-cyclopropyl; $R^1$ is $CH_2$-$A^1$; where $A^1$ in the definition of $R^1$ is phenyl, thienyl, thiazolyl, pyridyl or pyrimidyl which is optionally substituted with one to three substituents, each substituent being independently selected from the group consisting of F, Cl, Me, OMe, $CF_3$, $OCF_3$ and $OCF_2H$; and $R^3$ is phenyl-$CH_2$—O—$CH_2$—, phenyl-$(CH_2)_3$—, 3-indolyl-$CH_2$—, thienyl-$CH_2$—O—$CH_2$—, thiazolyl-$CH_2$—O—$CH_2$—, pyridyl-$CH_2$—O—$CH_2$—, pyrimidyl-$CH_2$—O—$CH_2$— or phenyl-O—$CH_2$—$CH_2$, where the aryl portion is optionally substituted with one to three substituents, each substituent being independently selected from the group consisting of F, Cl, Me, OMe, $CF_3$, $OCF_3$ and $OCF_2H$.

A group of compounds, which is preferred among the "$M^1$ Group" of compounds, designated the "N Group", contains those compounds of the "$M^1$ Group", having the formula (I) as shown hereinabove, wherein $X^5$ and $X^{5a}$ are each methyl; $R^2$ is methyl, ethyl, or —$CH_2CF_3$; $A^1$ is phenyl optionally substituted with one to three substituents, each substituent being independently selected from the group consisting of F, Cl, Me, OMe, $CF_3$, $OCF_3$ and $OCF_2H$; $R^3$ is phenyl-$CH_2$—O—$CH_2$—, phenyl-$(CH_2)_3$— or thienyl-$CH_2$—O—$CH_2$—; where the aryl portion is optionally substituted with one to three substituents, each substituent being independently selected from the group consisting of F, Cl, Me, OMe, $CF_3$, $OCF_3$ and $OCF_2H$.

Another group of compounds, which is preferred among the "$M^1$ Group" of compounds, designated the "0 Group", contains those compounds of the "M' Group", having the formula (I) as shown hereinabove, wherein $X^5$ and $X^{5a}$ are each methyl; $R^2$ is methyl, ethyl, or $CH_2CF_3$; $A^1$ is 2-pyridyl or 3-pyridyl optionally substituted with one to two substituents, each substituent being independently selected from the group consisting of F, Cl, Me, OMe, $CF_3$, $OCF_3$ and $OCF_2H$; $R^3$ is phenyl-$CH_2$—O—$CH_2$—, phenyl-$(CH_2)_3$— or thienyl-$CH_2$—O—$CH_2$—; where the aryl portion is optionally substituted with one to three substituents, each substituent being independently selected from the group consisting of F, Cl, Me, OMe, $CF_3$, $OCF_3$ and $OCF_2H$.

Another group of compounds, which is preferred among the "$M^1$ Group" of compounds, designated the "P Group", contains those compounds of the "$M^1$ Group", having the formula (I) as shown hereinabove, wherein $X^5$ and $X^{5a}$ are each methyl; $R^2$ is methyl, ethyl, or $CH_2CF_3$; $A^1$ is phenyl optionally substituted with one to three substituents, each substituent being independently selected from the group consisting of F, Cl, Me, OMe, $CF_3$, $OCF_3$ and $OCF_2H$; $R^3$ is 2-pyridyl-$CH_2$—O—$CH_2$—, or 3-pyridyl-$CH_2$—O—$CH_2$—; where the aryl portion is optionally substituted with one to two substituents, each substituent being independently selected from the group consisting of F, Cl, Me, OMe, $CF_3$, $OCF_3$ and $OCF_2H$.

A group of compounds, which is preferred among the "0 Group" of compounds, designated the "0 Group", contains those compounds of the "0 Group", having the formula:

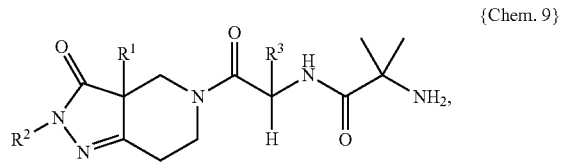

{Chem. 9} the racemic-diastereomeric mixtures and optical isomers of said compounds
wherein
$R^2$ is methyl; $A^1$ is 2-pyridyl; and $R^3$ is —$CH_2$—O—$CH_2$-phenyl;
$R^2$ is $CH_2CF_3$; $A^1$ is 2-pyridyl; and $R^3$ is —$CH_2$—O—$CH_2$-3-chloro-phenyl;
$R^2$ is $CH_2CF_3$; $A^1$ is 2-pyridyl; and $R^3$ is —$CH_2$—O—$CH_2$-4-chloro-phenyl;
$R^2$ is $CH_2CF_3$; $A^1$ is 2-pyridyl; and $R^3$ is —$CH_2$—O—$CH_2$-2,4-di-chloro-phenyl;
$R^2$ is $CH_2CF_3$; $A^1$ is 2-pyridyl; and $R^3$ is —$CH_2$—O—$CH_2$-3-chloro-thiophene; or
$R^2$ is $CH_2CF_3$; $A^1$ is 2-pyridyl; and $R^3$ is —$CH_2$—O—$CH_2$-2,4-di-fluoro-phenyl.

The diastereomeric mixture of 2-amino-N-[1-(R)-benzyloxymethyl-2-(2-methyl-3-oxo-3a-(R,S)-pyridin-2-ylm-ethyl-2,3,3a,4,6,7-hexahydro-pyrazolo[4,3-c]pyridin-5-yl)-2-oxo-ethyl]-2-methyl-propionamide is preferred among the "Q Group" of compounds and the separated 3a-(R) and 3a-(S) isomers are preferred of the diastereomeric mixture.

The diastereomeric mixture of 2-amino-N-{1-(R)-(3-chloro-benzyloxy-methyl)-2-oxo-2-[3-oxo-3a-(R,S)-pyridin-2-ylmethyl-2-(2,2,2-trifluoro-ethyl)-2,3,3a,4,6,7-hexahydro-pyrazolo[4,3-c]pyridin-5-yl]-ethyl}-2-methyl-propionamide is preferred among the "Q Group" of compounds and the separated 3a-(R) and 3a-(S) isomers are preferred of the diastereomeric mixture.

The diastereomeric mixture of 2-amino-N-{1-(R)-(4-chloro-benzyloxy-methyl)-2-oxo-2-[3-oxo-3a-(R,S)-pyridin-2-ylmethyl-2-(2,2,2-trifluoro-ethyl)-2,3,3a,4,6,7-hexahydro-pyrazolo[4,3-c]pyridin-5-yl]ethyl}-2-methyl-propionamide is preferred among the "Q Group" of compounds and the separated 3a-(R) and 3a-(S) isomers are preferred of the diastereomeric mixture.

The diastereomeric mixture of 2-amino-N-{1-(R)-(2,4-dichloro-benzyloxymethyl)-2-oxo-2-[3-oxo-3a-(R,S)-pyridin-2-ylmethyl-2-(2,2,2-trifluoro-ethyl)-2,3,3a,4,6,7-hexahydro-pyrazolo[4,3-q]pyridin-5-yl]-ethyl}-2-methyl-propionamide is preferred among the "Q Group" of compounds and the separated 3a-(R) and 3a-(S) isomers are preferred of the diastereomeric mixture.

The diastereomeric mixture of 2-amino-N-{1-(R)-(4-chloro-thiophen-2-ylmethoxymethyl)-2-oxo-2-[3-oxo-3a-(R,S)-pyridin-2-ylmethyl-2-(2,2,2-trifluoro-ethyl)-2,3,3a,4,5,7-hexahydro-pyrazolo[3,4-c]pyridin-6-yl]-ethyl}-2-methyl-propionamide is preferred among the "Q Group" of compounds and the separated 3a-(R) and 3a-(S) isomers are preferred of the diastereomeric mixture.

The diastereomeric mixture of 2-amino-N-{1-(R)-(2,4-difluoro-benzyloxy-methyl)-2-oxo-2-[3-oxo-3a-(R,S)-pyridin-2-ylmethyl-2-(2,2,2-trifluoro-ethyl)-2,3,3a,4,6,7-hexahydro-pyrazolo[4,3-c]pyridin-5-yl]-ethyl}-2-methyl-propionamide is preferred among the "Q Group" of compounds and the separated 3a-(R) and 3a-(S) isomers are preferred of the diastereomeric mixture.

The following compounds are preferable:

2-amino-N-(1-(3a-(R,S)-benzyl-2-methyl-3-oxo-2,3,3a,4,6,7-hexahydro-pyrazolo[4,3-c]pyridine-5-carbonyl)-4-phenyl(R)-butyl]-isobutyramide;

2-amino-N-1-(1-(3a-(R)-benzyl-2-methyl-3-oxo-2,3,3a,4,6,7-hexahydro-pyrazolo[4,3-c]pyridine-5-carbonyl)-4-phenyl(R)-butyl]-isobutyramide;

2-amino-N-[1-(3a-(S)-benzyl-2-methyl-3-oxo-2,3,3a,4,6,7-hexahydro-pyrazolo[4,3-c]pyridine-5-carbonyl)-4-phenyl(R)-butyl]-isobutyramide;

2-amino-N-[2-(3a-(R,S)-benzyl-2-methyl-3-oxo-2,3,3a,4,6,7-hexahydro-pyrazolo[4,3-c]pyridin-5-yl)-1-(R)-(1H-indol-3-ylmethyl)-2-oxo-ethyl]-isobutyramide;

2-amino-N-[2-(3a-(R)-benzyl-2-methyl-3-oxo-2,3,3a,4,6,7-hexahydro-pyrazolo[4,3-c]pyridin-5-yl)-1-(R)-(1H-indol-3-ylmethyl)-2-oxo-ethyl]-isobutyramide;

2-amino-N-[2-(3a-(S)-benzyl-2-methyl-3-oxo-2,3,3a,4,6,7-hexahydro-pyrazolo[4,3-c]pyridin-5-yl)-1-(R)-(1H-indol-3-ylmethyl)-2-oxo-ethyl]-isobutyramide;

2-amino-N-[2-(3a-(R,S)-benzyl-2-ethyl-3-oxo-2,3,3a,4,6,7-hexahydro-pyrazolo[4,3-c]pyridin-5-yl)-1-(R)-(1H-indol-3-ylmethyl)-2-oxo-ethyl]-isobutyramide;

2-amino-N-[2-(3a-(R)-benzyl-2-ethyl-3-oxo-2,3,3a,4,6,7-hexahydro-pyrazolo[4,3-c]pyridin-5-yl)-1-(R)-(1H-indol-3-ylmethyl)-2-oxo-ethyl]isobutyramide;

2-amino-N-[2-(3a-(S)-benzyl-2-ethyl-3-oxo-2,3,3a,4,6,7-hexahydro-pyrazolo[4,3-c]pyridin-5-yl)-1-(R)-(1H-indol-3-ylmethyl)-2-oxo-ethyl]-isobutyramide;

2-amino-N-[2-(3a-(R,S)-(4-fluoro-benzyl)-2-methyl-3-oxo-2,3,3a,4,6,7-hexahydro-pyrazolo[4,3-c]pyridin-5-yl)-1-(R)-(1H-indol-3-ylmethyl)-2-oxo-ethyl]-isobutyramide;

2-amino-N-[2-(3a-(R)-(4-fluoro-benzyl)-2-methyl-3-oxo-2,3,3a,4,6,7-hexahydro-pyrazolo[4,3-c]pyridin-5-yl)-1-(R)-(1H-indol-3-ylmethyl)-2-oxo-ethyl]-isobutyramide;

2-amino-N-[2-(3a-(S)-(4-fluoro-benzyl)-2-methyl-3-oxo-2,3,3a,4,6,7-hexahydro-pyrazolo[4,3-c]pyridin-5-yl)-1-(R)-(1H-indol-3-ylmethyl)-2-oxo-ethyl]-isobutyramide;

2-amino-N-[2-(3a-(R,S)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide;

2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide;

2-amino-N-[2-(3a-(S)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide;

2-amino-N-[2-(3a-(R,S)-benzyl-2-ethyl-3-oxo-2,3,3a,4,6,7-hexahydro-pyrazolo[4,3-c]pyridin-5-yl)-1-(R)-benzyloxymethyl-2-oxo-ethyl]-isobutyramide;

2-amino-N-[2-(3a-(R)-benzyl-2-ethyl-3-oxo-2,3,3a,4,6,7-hexahydro-pyrazolo[4,3-c]pyridin-5-yl)-1-(R)-benzyloxymethyl-2-oxo-ethyl]-isobutyramide;

2-amino-N-[2-(3a-(S)-benzyl-2-ethyl-3-oxo-2,3,3a,4,6,7-hexahydro-pyrazolo[4,3-c]pyridin-5-yl)-1-(R)-benzyloxymethyl-2-oxo-ethyl]-isobutyramide;

2-amino-N-[2-(3a-(R,S)-benzyl-3-oxo-2-(2,2,2-trifluoro-ethyl)-2,3,3a,4,6,7-hexahydro-pyrazolo[4,3-c]pyridin-5-yl)-1-(R)-benzyloxymethyl-2-oxo-ethyl]-isobutyramide;

2-amino-N-[2-(3a-(R)-benzyl-3-oxo-2-(2,2,2-trifluoro-ethyl)-2,3,3a,4,6,7-hexahydro-pyrazolo[4,3-c]pyridin-5-yl)-1-(R)-benzyloxymethyl-2-oxo-ethyl]-isobutyramide;

2-amino-N-[2-(3a-(S)-benzyl-3-oxo-2-(2,2,2-trifluoro-ethyl)-2,3,3a,4,6,7-hexahydro-pyrazolo[4,3-c]pyridin-5-yl)-1-(R)-benzyloxymethyl-2-oxo-ethyl]-isobutyramide;

2-amino-N-[1-(R)-benzyloxymethyl-2-(3a-(R,S)-(4-fluoro-benzyl)-2-methyl-3-oxo-2,3,3a,4,6,7-hexahydro-pyrazolo[4,3-c]pyridin-5-yl)-2-oxo-ethyl]-isobutyramide;

2-amino-N-[1-(R)-benzyloxymethyl-2-(3a-(R)-(4-fluoro-benzyl)-2-methyl-3-oxo-2,3,3a,4,6,7-hexahydro-pyrazolo[4,3-c]pyridin-5-yl)-2-oxo-ethyl]isobutyramide;

2-amino-N-[1-(R)-benzyloxymethyl-2-(3a-(S)-(4-fluoro-benzyl)-2-methyl-3-oxo-2,3,3a,4,6,7-hexahydro-pyrazolo[4,3-c]pyridin-5-yl)-2-oxo-ethyl]-isobutyramide;

2-amino-N-[2-(3a-(R,S)-benzyl-2-tert-butyl-3-oxo-2,3,3a,4,6,7-hexahydro-pyrazolo[4,3-c]pyridin-5-yl)-1-(R)-benzyloxymethyl-2-oxo-ethyl]-isobutyramide;

2-amino-N12-(3a-(R)-benzyl-2-tert-butyl-3-oxo-2,3,3a,4,6,7-hexahydro-pyrazolo[4,3-c]pyridin-5-yl)-1-(R)-benzyloxymethyl-2-oxo-ethyl]-isobutyramide;

2-amino-N-[2-(3a-(S)-benzyl-2-tert-butyl-3-oxo-2,3,3a,4,6,7-hexahydro-pyrazolo[4,3-c]pyridin-5-yl)-1-(R)-benzyloxymethyl-2-oxo-ethyl]-isobutyramide;

2-amino-N-[2-(3a-(R,S)-benzyl-3-oxo-2,3,3a,4,6,7-hexahydro-pyrazolo[4,3-c]pyridin-5-yl)-1-(R)-benzyloxymethyl-2-oxo-ethyl]-isobutyramide;

2-amino-N-[2-(3a-(R)-benzyl-3-oxo-2,3,3a,4,6,7-hexahydro-pyrazolo[4,3-c]pyridin-5-yl)-1-(R)-benzyloxymethyl-2-oxo-ethyl]-isobutyramide;

2-amino-N-[2-(3a-(S)-benzyl-3-oxo-2,3,3a,4,6,7-hexahydro-pyrazolo[4,3-c]pyridin-5-yl)-1-(R)-benzyloxymethyl-2-oxo-ethyl]-isobutyramide;

2-amino-N-[1-(R)-benzyloxymethyl-2-(2-methyl-3-oxo-3a-(R,S)-pyridin-2-ylmethyl-2,3,3a,4,6,7-hexahydro-pyrazolo[4,3-c]pyridin-5-yl)-2-oxo-ethyl]-2-methyl-propionamide;

2-amino-N-[1-(R)-benzyloxymethyl-2-(2-methyl-3-oxo-3a-(R)-pyridin-2-ylmethyl-2,3,3a,4,6,7-hexahydro-pyrazolo[4,3-c]pyridin-5-yl)-2-oxo-ethyl]-2-methyl-propionamide;

2-amino-N-[1-(R)-benzyloxymethyl-2-(2-methyl-3-oxo-3a-(S)-pyridin-2-ylmethyl-2,3,3a,4,6,7-hexahydro-pyrazolo[4,3-c]pyridin-5-yl)-2-oxo-ethyl]-2-methyl-propionamide;

2-amino-N-[1-(R)-(3-chloro-benzyloxymethyl)-2-oxo-2-(3-oxo-3a-(R,S)-pyridin-2-ylmethyl-2-(2,2,2-trifluoro-ethyl)-2,3,3a,4,6,7-hexahydro-pyrazolo[4,3-c]pyridin-5-yl)-ethyl]-2-methyl-propionamide;

2-amino-N-[1-(R)-(3-chloro-benzyloxymethyl)-2-oxo-2-(3-oxo-3a-(R)-pyridin-2-ylmethyl-2-(2,2,2-trifluoro-ethyl)-2,3,3a,4,6,7-hexahydro-pyrazolo[4,3-c]pyridin-5-yl)-ethyl]-2-methyl-propionamide;

2-amino-N-[1-(R)-(3-chloro-benzyloxymethyl)-2-oxo-2-(3-oxo-3a-(S)-pyridin-2-ylmethyl-2-(2,2,2-trifluoro-ethyl)-2,3,3a,4,6,7-hexahydro-pyrazolo[4,3-c]pyridin-5-yl)-ethyl]-2-methyl-propionamide;

2-amino-N-[1-(R)-(4-chloro-benzyloxymethyl)-2-oxo-2-(3-oxo-3a-(R,S)-pyridin-2-ylmethyl-2-(2,2,2-trifluoro-ethyl)-2,3,3a,4,6,7-hexahydro-pyrazolo[4,3-c]pyridin-5-yl)-ethyl]-2-methyl-propionamide;

2-amino-N-[1-(R)-(4-chloro-benzyloxymethyl)-2-oxo-2-(3-oxo-3a-(R)-pyridin-2-ylmethyl-2-(2,2,2-trifluoro-ethyl)-2,3,3a,4,6,7-hexahydro-pyrazolo[4,3-c]pyridin-5-yl)-ethyl]-2-methyl-propionamide;

2-amino-N-[1-(R)-(4-chloro-benzyloxymethyl)-2-oxo-2-(3-oxo-3a-(S)-pyridin-2-ylmethyl-2-(2,2,2-trifluoro-ethyl)-

2,3,3a,4,6,7-hexahydro-pyrazolo[4,3-c]pyridin-5-yl)-ethyl]-2-methyl-propionamide;

2-amino-N-[1-(R)-(2,4-dichloro-benzyloxymethyl)-2-oxo-2-(3-oxo-3a-(R,S)-pyridin-2-ylmethyl-2-(2,2,2-trifluoro-ethyl)-2,3,3a,4,6,7-hexahydro-pyrazolo[4,3-c]pyridin-5-yl)-ethyl]-2-methyl-propionamide;

2-amino-N-[1-(R)-(2,4-dichloro-benzyloxymethyl)-2-oxo-2-(3-oxo-3a-(R)-pyridin-2-ylmethyl-2-(2,2,2-trifluoro-ethyl)-2,3,3a,4,6,7-hexahydro-pyrazolo[4,3-c]pyridin-5-yl)-ethyl]-2-methyl-propionamide;

2-amino-N-[1-(R)-(2,4-dichloro-benzyloxymethyl)-2-oxo-2-(3-oxo-3a-(S)-pyridin-2-ylmethyl-2-(2,2,2-trifluoro-ethyl)-2,3,3a,4,6,7-hexahydro-pyrazolo[4,3-c]pyridin-5-yl)-ethyl]-2-methyl-propionamide;

2-amino-N-[1-(R)-(4-chloro-thiophen-2-ylmethoxymethyl)-2-oxo-2-(3-oxo-3a-(R,S)-pyridin-2-ylmethyl-2-(2,2,2-trifluoro-ethyl)-2,3,3a,4,5,7-hexahydro-pyrazolo[3,4-c]pyridin-6-yl)-ethyl]-2-methyl-propionamide;

2-amino-N-[1-(R)-(4-chloro-thiophen-2-ylmethoxymethyl)-2-oxo-2-(3-oxo-3a-(R)-pyridin-2-ylmethyl-2-(2,2,2-trifluoro-ethyl)-2,3,3a,4,5,7-hexahydro-pyrazolo[3,4-c]pyridin-6-yl)-ethyl]-2-methyl-propionamide;

2-amino-N-[1-(R)-(4-chloro-thiophen-2-ylmethoxymethyl)-2-oxo-2-(3-oxo-3a-(S)-pyridin-2-ylmethyl-2-(2,2,2-trifluoro-ethyl)-2,3,3a,4,5,7-hexahydro-pyrazolo[3,4-c]pyridin-6-yl)-ethyl]-2-methyl-propionamide;

2-amino-N-[1-(R)-(2,4-difluoro-benzyloxymethyl)-2-oxo-2-(3-oxo-3a-(R,S)-pyridin-2-ylmethyl-2-(2,2,2-trifluoro-ethyl)-2,3,3a,4,6,7-hexahydro-pyrazolo[4,3-c]pyridin-5-yl)-ethyl]-2-methyl-propionamide;

2-amino-N-[1-(R)-(2,4-difluoro-benzyloxymethyl)-2-oxo-2-(3-oxo-3a-(R)-pyridin-2-ylmethyl-2-(2,2,2-trifluoro-ethyl)-2,3,3a,4,6,7-hexahydro-pyrazolo[4,3-c]pyridin-5-yl)-ethyl]-2-methyl-propionamide;

2-amino-N-[1-(R)-(2,4-difluoro-benzyloxymethyl)-2-oxo-2-(3-oxo-3a-(S)-pyridin-2-ylmethyl-2-(2,2,2-trifluoro-ethyl)-2,3,3a,4,6,7-hexahydro-pyrazolo[4,3-c]pyridin-5-yl)-ethyl]-2-methyl-propionamide;

2-amino-N-[2-(3a-(R,S)-benzyl-2-methyl-3-oxo-2,3,3a,4,6,7-hexahydro-pyrazolo[4,3-c]pyridin-5-yl)-1-(R)-(3,4-difluoro-benzyloxymethyl)-2-oxo-ethyl]-2-methyl-propionamide;

2-amino-N-[2-(3a-(R)-benzyl-2-methyl-3-oxo-2,3,3a,4,6,7-hexahydro-pyrazolo[4,3-c]pyridin-5-yl)-1-(R)-(3,4-difluoro-benzyloxymethyl)-2-oxo-ethyl]-2-methyl-propionamide; and 2-amino-N-[2-(3a-(S)-benzyl-2-methyl-3-oxo-2,3,3a,4,6,7-hexahydro-pyrazolo[4,3-c]pyridin-5-yl)-1-(R)-(3,4-difluoro-benzyloxymethyl)-2-oxo-ethyl]-2-methyl-propionamide.

The following compounds are more preferable:

2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide; and 2-amino-N-[1-(R)-(2,4-difluoro-benzyloxymethyl)-2-oxo-2-(3-oxo-3a-(R)-pyridin-2-ylmethyl-2-(2,2,2-trifluoro-ethyl)-2,3,3a,4,6,7-hexahydro-pyrazolo[4,3-c]pyridin-5-yl)-ethyl]-2-methyl-propionamide.

In the above structural formulae and throughout the instant application, the following terms have the indicated meanings unless expressly stated otherwise:

The alkyl groups are intended to include those alkyl groups of the designated length in either a straight or branched configuration which may optionally contain double or triple bonds. Exemplary of such alkyl groups are methyl, ethyl, propyl, isopropyl, butyl, sec-butyl, tertiary butyl, pentyl, isopentyl, hexyl, isohexyl, allyl, ethynyl, propenyl, butadienyl, hexenyl and the like.

When the definition $C_o$-alkyl occurs in the definition, it means a single covalent bond.

The alkoxy groups specified above are intended to include those alkoxy groups of the designated length in either a straight or branched configuration. Exemplary of such alkoxy groups are methoxy, ethoxy, propoxy, isopropoxy, butoxy, isobutoxy, tertiary butoxy, pentoxy, isopentoxy, hexoxy, isohexoxy, allyloxy, 2-propynyloxy, isobutenyloxy, hexenyloxy and the like.

The term "halogen" or "halo" is intended to include the halogen atoms fluorine, chlorine, bromine and iodine.

The term "halogenated alkyl" is intended to include an alkyl group as defined hereinabove substituted by one or more halogen atoms as defined hereinabove.

The term "halogenated cycloalkyl" is intended to include a cycloalkyl group substituted by one or more halogen atoms as defined hereinabove.

The term "aryl" is intended to include phenyl and naphthyl and aromatic 5- and 6-membered rings with 1 to 4 heteroatoms or fused 5- or 6-membered bicyclic rings with 1 to 4 heteroatoms of nitrogen, sulfur or oxygen. Examples of such heterocyclic aromatic rings are pyridine, thiophene (also known as thienyl), furan, benzothiophene, tetrazole, indole, N-methylindole, dihydroindole, indazole, N-formylindole, benzimidazole, thiazole, pyrimidine, and thiadiazole.

Those skilled in the arts will recognize that certain combinations of heteroatom-containing substituents listed in this invention define compounds which will be less stable under physiological conditions (e.g., those containing acetal or aminal linkages). Accordingly, such compounds are less preferred.

The expression "prodrug" refers to compounds that are drug precursors, which following administration, release the drug in vivo via some chemical or physiological process (e.g., a prodrug on being brought to the physiological pH is converted to the desired drug form). Exemplary prodrugs upon cleavage release the corresponding free acid, and such hydrolyzable ester-forming residues of the compounds of this invention include but are not limited to carboxylic acid substituents (e.g., $R^1$ is —$(CH_2)_qC(O)_2X^6$ where $X^6$ is hydrogen, or $R^2$ or $A^1$ contains carboxylic acid) wherein the free hydrogen is replaced by $(C_1$-$C_4)$alkyl, $(C_2$-$C_{12})$alkanoyloxymethyl, $(C_4$-$C_9)$1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1$-$C_2)$alkylamino$(C_2$-$C_3)$alkyl (such as β-dimethylaminoethyl), carbamoyl-$(C_1$-$C_2)$alkyl, N,N-di$(C_1$-$C_2)$-alkylcarbamoyl-$(C_1$-$C_2)$alkyl and piperidino-, pyrrolidino- or morpholino$(C_2$-$C_3)$alkyl.

Other exemplary prodrugs release an alcohol of Formula (I) wherein the free hydrogen of the hydroxyl substituent (e.g., $R^1$ contains hydroxyl) is replaced by $(C_1$-$C_6)$alkanoyloxymethyl, 1-(($C_1$-$C_6)$alkanoyloxy)ethyl, 1-methyl-1-(($C_1$-$C_6)$alkanoyloxy)ethyl, $(C_1$-$C_6)$alkoxycarbonyloxymethyl, N—$(C_1$-$C_6)$alkoxycarbonylaminomethyl, succinoyl, $(C_1$-$C_6)$alkanoyl, α-amino$(C_1$-$C_4)$alkanoyl, arylacetyl and α-aminoacyl, or α-aminoacyl-α-aminoacyl wherein said α-aminoacyl moieties are independently any of the naturally occurring L-amino acids found in proteins, $P(O)(OH)_2$, —$P(O)(O(C_1-C_6)alkyl)_2$ or glycosyl (the radical resulting from detachment of the hydroxyl of the hemiacetal of a carbohydrate).

Prodrug of this invention includes amino substituents wherein when $R^7$ or $R^8$ is hydrogen, the free hydrogen is replaced by $(C_2-C_{12})$alkanoyloxymethyl, $(C_4-C_9)$1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di $(C_1-C_2)$-alkylcarbamoyl-$(C_1-C_2)$alkyl and piperidino-, pyrrolidino- or morpholino$(C_2-C_3)$alkyl.

Prodrugs of this invention where a carboxyl group in a carboxylic acid of the formula (I) is replaced by an ester may be prepared by combining the carboxylic acid with an appropriate alkyl halide in the presence of a base such as potassium carbonate in an inert solvent such as DMF at a temperature of about 0° C. to 100° C. for about 1 to about 24 hours. Alternatively, the acid is combined with an appropriate alcohol as solvent in the presence of a catalytic amount of an acid such as concentrated sulfuric acid at a temperature of about 20° C. to 120° C., preferably at reflux, for about 1 hour to about 24 hours. Another method is the reaction of the acid in an inert solvent such as THF, with concomitant removal of the water being produced by physical (e.g., Dean Stark trap) or chemical (e.g., molecular sieves) means.

Prodrugs of this invention where an alcohol function has been derivatized as an ether may be prepared by combining the alcohol with an appropriate alkyl bromide or iodide in the presence of a base such as potassium carbonate in an inert solvent such as DMF at a temperature of about 0° C. to 100° C. for about 1 to about 24 hours. Alkanoylaminomethyl ethers may be obtained by reaction of the alcohol with a bis-(alkanoylamino)methane in the presence of a catalytic amount of an acid in an inert solvent such as THF, according to a method described in U.S. Pat. No. 4,997,984. Alternatively, these compounds may be prepared by the methods described by Hoffman et al. in J. Org. Chem. 1994, 59, p. 3530.

Certain of the above defined terms may occur more than once in the above formula and upon such occurrence each term shall be defined independently of the other.

The compounds of the instant invention all have at least one asymmetric center as noted by the asterisk in the structural formula (I) above. Additional asymmetric centers may be present on the molecule depending upon the nature of the various substituents on the molecule. Each such asymmetric center will produce two optical isomers and it is intended that all such optical isomers, as separated, pure or partially purified optical isomers, racemic mixtures or diastereomeric mixtures thereof, be included within the scope of the instant invention. In the case of the asymmetric center represented by the asterisk, it has been found that the absolute stereochemistry of the more active and thus more preferred isomer is shown in the formula (IA). This preferred absolute configuration also applies to the formula (I).

(IA)

{Chem. 10}

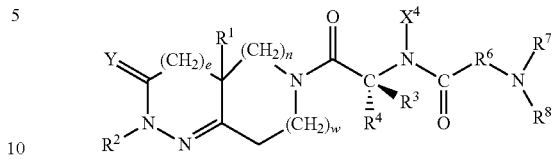

With the $R^4$ substituent as hydrogen, the spatial configuration of the asymmetric center corresponds to that in a D-amino acid. In most cases this is also designated an R-configuration although this will vary according to the values of $R^3$ and $R^4$ used in making R- or S-stereochemical assignments.

The instant compounds are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, D-tartaric, L-tartaric, malonic, methane sulfonic acids and the like. In addition, certain compounds containing an acidic function such as a carboxy can be isolated in the form of their inorganic salt in which the counter-ion can be selected from sodium, potassium, lithium, calcium, magnesium and the like, as well as from organic bases.

The pharmaceutically acceptable salts are formed by taking about 1 equivalent of a compound of the formula (I) and contacting it with about 1 equivalent of the appropriate corresponding acid of the salt which is desired. Work-up and isolation of the resulting salt is well-known to those of ordinary skill in the art. For a review on suitable salts, see "Handbook of Pharmaceutical Salts: Properties, Selection, and Use" by Stahl and Wermuth (Wiley-VCH, Weinheim, Germany, 2002).

The compounds of the invention may exist in both unsolvated and solvated forms.

The term "solvate" is used herein to describe a molecular complex comprising the compound of the invention and one or more pharmaceutically acceptable solvent molecules, for example, ethanol.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized. For a review of such complexes, see J Pharm Sci, 64 (8), 1269-1288 by Haleblian (August 1975).

All references to compounds of the present invention include references to salts, solvates and complexes thereof and to solvates and complexes of salts thereof.

The compounds of the invention include compounds of the present invention as hereinbefore defined, polymorphs, prodrugs, and isomers thereof (including optical, geometric and tautomeric isomers) and isotopically-labeled compounds of the present invention as hereinafter defined.

As stated above, the invention includes all polymorphs of the compounds of the present invention as hereinbefore defined.

Compounds of the present invention containing one or more asymmetric carbon atoms can exist as two or more stereoisomers. Where a compound of the present invention contains an alkenyl or alkenylene group, geometric cis/trans (or Z/E) isomers are possible. Where the compound contains, for example, a keto or oxime group or an aromatic moiety, tautomeric isomerism ('tautomerism') can occur. It follows that a single compound may exhibit more than one type of isomerism.

Included within the scope of the present invention are all stereoisomers, geometric isomers and tautomeric forms of the compounds of the present invention, including compounds exhibiting more than/equal to two types of isomerism, and mixtures of one or more thereof. Also included are acid addition salts or base salts wherein the counter ion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallization. Conventional techniques for the preparation/isolation of individual enantiomers include chiral synthesis from a suitable optically pure precursor and resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of the present invention contains an acidic or basic moiety, an acid or base such as tartaric acid or 1-phenylethylamine. The resulting diastereomeric mixture may be separated by chromatography and/or fractional crystallization and one or both of the diastereoisomers can be converted to the corresponding pure enantiomer(s) by means well known to a skilled person.

Chiral compounds of the present invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50 (w/w) % isopropanol, typically from 2 to 20 (w/w) %, and from 0 to 5 (w/w) % of an alkylamine, typically 0.1 (w/w) % diethylamine. Concentration of the eluate affords the enriched mixture.

Stereoisomeric conglomerates may be separated by conventional techniques known to those skilled in the art—see, for example, *Stereochemistry of Organic Compounds* by E L Eliel (Wiley, New York, 1994).

The present invention includes all pharmaceutically acceptable isotopically-labeled compounds of the present invention wherein one or more atoms are replaced by atoms having the same atomic number, but an atomic mass or mass number different from the atomic mass or mass number usually found in nature.

Examples of isotopes suitable for inclusion in the compounds of the present invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

Certain isotopically-labeled compounds of the present invention, for example, those incorporating a radioactive isotope, are useful in drug and/or substrate tissue distribution studies associated with cancer therapy which includes diagnosis, alleviation of symptoms, improvement of QOL, and prophylaxis. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of the present invention can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the present invention include those wherein the solvent for crystallization may be isotopically substituted, e.g. D$_2$O, d$_6$-acetone, d$_6$-DMSO.

Compounds of the present invention intended for pharmaceutical use may be administered as crystalline or amorphous products. They may be obtained, for example, as solid plugs, powders, or films by methods such as precipitation, crystallization, freeze drying, spray drying, and evaporative drying. Microwave or radio frequency drying may be used for this purpose.

The compounds of this invention can be administered by oral, parenteral (e.g., intramuscular, intraperitoneal, intravenous or subcutaneous injection, or transplant), nasal, vaginal, rectal, sublingual, or topical routes of administration and can be formulated with pharmaceutically acceptable carriers to provide dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, and starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

Formulations for topical administration in the mouth, for example buccally or sublingually, include lozenges comprising the active ingredient in a flavored base such as sucrose and acacia or tragacanth, and pastilles comprising the active ingredient in a base such as gelatin and glycerin or sucrose and acacia.

The compounds of the present invention or a pharmaceutically acceptable salt thereof may also be formulated as depot preparations. Such long acting formulations may be administered by transplantation (for example subcutaneously or intramuscularly) or by intramuscular injection. Thus, for example, the compounds of the present invention may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may contain other agents conventional in the art in the light of the type of formulation in question, for example those suitable for oral administration such as flavoring agents.

The dosage of active ingredient in the compositions of this invention may be varied; however, it is necessary that the amount of the active ingredient be such that a suitable dosage form is obtained. The selected dosage depends upon the desired therapeutic efficacy, on the route of administration, and on the duration of the treatment. Generally, dosage levels of between 0.0001 to 100 mg/kg of body weight daily are administered to humans and other animals, e.g., mammals, to obtain effective release of growth hormone.

A preferred dosage range is 0.01 to 5.0 mg/kg of body weight daily which can be administered as a single dose or divided into multiple doses.

The compound (I) or a salt thereof of the present invention (hereinafter referred to as compound of the present invention) have an ameliorating effect on cachexia, that is, the activity to ameliorate the systemic syndrome which is associated with progressive loss of body weight (inclusive of weight loss due to lipolysis and weight loss due to myolysis), anemia, edema, and anorexia as cardinal symptoms and which develops in chronic diseases such as malignant tumor, tuberculosis, diabetes, hemodyscrasia, endocrine disease, chronic obstructive pulmonary disease, chronic kidney disease, cardiac failure, infectious disease, and acquired immunodeficiency syndrome. In addition, the toxic potential of the compound of the present invention is low. The therapeutic agent of the present invention can be used as an agent for the treatment of cachexia or malnutrition in mammals (e.g. human, mouse, rat, rabbit, dog, cat, bovine, horse, pig, monkey, etc.). The cachexia is, for example, cancer cachexia, tuberculous cachexia, diabetic cachexia, hemodyscrasia-associated cachexia, endocrine disease-associated cachexia, chronic obstructive pulmonary disease-associated cachexia, chronic kidney disease-associated cachexia, cardiac failure-associated cachexia, infectious disease-associated cachexia, or acquired immunodeficiency syndrome-associated cachexia. The therapeutic agent of the present invention can be used preferably in cachexia associated with malignant tumor, especially a carcinoma.

As the therapeutic agent of the present invention, the compound of the present invention may be used as it is, but the compound is usually used in the form of a pharmaceutical composition obtained by mixing the compound with a pharmaceutically acceptable carrier or the like known per se. The pharmaceutically acceptable carrier herein is a variety of organic or inorganic carriers in common use as raw materials for pharmaceutical preparations, and such carriers are employed as an excipient, lubricant, binder, disintegrator, etc. for a solid dosage form; or a solvent, solubilizer, suspending agent, tonicity agent, buffering agent, analgesic, etc. for a liquid dosage form. Where necessary, pharmaceutical additives such as a preservative, antioxidant, coloring agent, sweetener, etc. can also be used. Preferred excipients include, for example, lactose, sucrose, D-mannitol, starch, crystalline cellulose, light silicic anhydride, etc. Preferred lubricants include, for example, magnesium stearate, calcium stearate, talc, colloidal silica, etc. Preferred binders include, for example, crystalline cellulose, sucrose, D-mannitol, trehalose, dextrin, hydroxypropylcellulose, hydroxypropylmethylcellulose, polyvinylpyrrolidone, etc. Preferred disintegrators include, for example, starch, carboxymethylcellulose, carboxymethylcellulose calcium, croscarmellose sodium, carboxymethylstarch sodium, etc.

Preferred solvents include, for example, water for injection, alcohol, propylene glycol, macrogol, sesame oil, corn oil, tricaprylin, etc. Preferred solubilizers include, for example, polyethylene glycol, propylene glycol, D-mannitol, trehalose, benzyl benzoate, ethanol, trisaminomethane, cholesterol, triethanolamine, sodium carbonate, sodium citrate, etc. Preferred suspending agents include, for example, surfactants such as stearyltriethanolamine, sodium lauryl sulfate, laurylaminopropionic acid, lecithin, benzalkonium chloride, benzethonium chloride, and glyceryl monostearate; and hydrophilic polymers such as polyvinyl alcohol, polyvinylpyrrolidone, carboxymethylcellulose sodium, methylcellulose, hydroxymethylcellulose, hydroxyethylcellulose, and hydroxypropylcellulose. Preferred tonicity agents include, for example, sodium chloride, glycerin, D-mannitol, etc. Preferred buffering agents include, for example, buffer solutions such as phosphate, acetate, carbonate, and citrate. Preferred analgesics include, for example, benzyl alcohol. Preferred preservatives include, for example, p-hydroxybenzoic esters, chlorobutanol, benzyl alcohol, phenethyl alcohol, dehydroacetic acid, sorbic acid, etc. Preferred antioxidants include, for example, sulfurous acid salts, ascorbic acid, etc.

When the compound of the present invention is used for the treatment of cachexia which develops in chronic diseases such as malignant tumor, tuberculosis, diabetes, hemodyscrasia, endocrine disease, chronic obstructive pulmonary disease, chronic kidney disease, cardiac failure, infectious disease, and acquired immunodeficiency syndrome, one or more different compounds having agonistic activities against the ghrelin receptor can be advantageously combined with another pharmacologically active compound (a second active agent).

The therapeutic agent of the present invention can be administered together with another drug such as a chemotherapeutic agent and an immunotherapeutic agent as the second active agent to a single subject, either concurrently or at staggered times. The dosages of these drugs can be appropriately selected by referring to the recommended clinical dose ranges. The mixing ratio of the therapeutic agent of the present invention and another drug can be appropriately selected according to the subject, age and body weight of the subject, current clinical status, administration time, dosage form, method of administration, and combination of drugs, among other factors. Preferred chemotherapeutic agents include, for example, alkylating agents (e.g. cyclophosphamide, ifosfamide), antimetabolites (e.g. methotrexate, 5-fluorouracil), antitumor antibiotics (e.g. mitomycin, adriamycin), plant-derived anticancer drugs (e.g. vincristine, vindesine, Taxol), cisplatin, carboplatin, and etoposide.

Particularly preferred are Furtulon and NeoFurtulon, which are 5-fluorouracil derivatives. Preferred immunotherapeutic agents include, for example, fungal or bacterial components (e.g. muramyl dipeptide derivatives, Picibanil), immunostimulant polysaccharides (e.g. lentinan, sizofuran, Krestin), recombinant cytokines (e.g. interferons, interleukins (IL)), and colony stimulating factors (e.g. granulocyte colony stimulating factor, erythropoietin). Particularly preferred are IL-1, IL-2, and IL-12.

Furthermore, drugs which are documented as having an ameliorating effect on cachexia in an animal model or clinical practice may also be used together with the therapeutic agent of the present invention and such drugs are exemplified by cyclooxygenase inhibitors (e.g. indomethacin) [Cancer Research, 49, 5935-5939, 1989], progesterone derivatives (e.g. megestrol acetate) [Journal of Clinical Oncology, 12, 213-225, 1994], glucocorticoids (e.g. dexamethasone), metoclopramides, tetrahydrocannabinols (the same literature as above), lipid metabolism improving agents (e.g. eicosapentaenoic acid) [British Journal of Cancer, 68, 314-318, 1993], growth hormone, IGF-1, and antibodies against the cachexia-inducing factors such as TNF-α, LIF, IL-6, and oncostatin M, and the like. The compound of the present invention can be used in combination with a diuretic. In this case, the administration time of the compound of the present invention and the diuretic are not limited, and they can be administered to a single subject, either concurrently or at staggered times. The dosage of the diuretic can be appropriately selected by referring to the recommended clinical dose ranges. The mixing ratio of the compound of the present invention and the diuretic can be appropriately selected according to the subject, age and body weight of the subject, current clinical status, administration time, dosage form, method of administration, and combination, among other factors. For example, when the subject is a human, the diuretic is used in a proportion of usually about 0.01 to about 100 weight parts, preferably about 0.1 to about 20 weight parts, relative to one weight part of the compound of the present invention. The diuretic includes, for example, xanthine derivative preparations (e.g. theobromine sodium salicylate, theobromine calcium salicylate), thiazide preparations (e.g. ethiazide, cyclopenthiazide, trichlormethiazide, hydrochlorothiazide, hydroflumethiazide, benzylhydrochlorothiazide, penflutizide, polythiazide, methyclothiazide), antialdosterone preparations (e.g. spironolactone, triamterene), carbonate dehydratase inhibitors (e.g. acetazolamide), chlorobenzenesulfonamide preparations (e.g. chlorthalidone, mefruside, indapamide), azosemide, isosorbide, ethacrynic acid, piretanide, bumetanide, and furosemide.

A kit for the treatment of cachexia, which comprises the compound of the present invention, or a pharmaceutically acceptable salt thereof, is also one aspect of the invention. A commercial package comprising a pharmaceutical composition containing the compound of the present invention, or a pharmaceutically acceptable salt thereof, and a written matter associated with said pharmaceutical composition, wherein the written matter stating that said pharmaceutical composition can or should be used for treating cachexia which develops in chronic diseases such as malignant tumor, tuberculosis, diabetes, hemodyscrasia, endocrine disease, chronic obstructive pulmonary disease, chronic kidney disease, cardiac failure, infectious disease, and acquired immunodeficiency syndrome, is also one aspect of the invention.

The term "treating" or "treatment", as used herein, refers to reversing, alleviating, inhibiting the progress of, or preventing the disorder or condition to which such term applies, or one or more symptoms of such disorder or condition. The term "treating" or "treatment", as used herein, includes not only the treatment of cachexia but also alleviation of symptoms, improvement of QOL, and prophylaxis. Therefore it includes "therapeutic agent" and "prophylactic agent".

Other features and advantages of the invention may be apparent from the following detailed description and the claims. Although particular embodiments of the present invention have been described, various other known or usual changes and modifications in this field fall into the present invention and are within the claims. The present invention also includes the equivalents, changes, uses, or variations, which are from the spirit of the present invention.

The compound of the present invention is administered in an amount sufficient to enhance the desired therapeutic efficacy on cachexia which develops in chronic diseases such as malignant tumor, tuberculosis, diabetes, hemodyscrasia, endocrine disease, chronic obstructive pulmonary disease, chronic kidney disease, cardiac failure, infectious disease, and acquired immunodeficiency syndrome.

Such a therapeutic effective amount varies in accordance with the specific condition to be treated, the patient's condition, the route of administration, the formulation, the judgement of the practitioner, and other factors. In the light of the disclosure, depending on the things known to those skilled in the art, the amount is decided by routine optimization techniques.

A therapeutic composition can comprise the compound of the present invention, or a pharmaceutically acceptable salt thereof. Such medicaments are mixed with a pharmaceutically acceptable transport medium or carrier.

As used herein, the pharmaceutically acceptable transport medium includes solvents, dispersion media, coatings, antibacterial and antifungal agents, tonicity and absorption delaying agents, and the like, compatible with pharmaceutical administration. The above medium may also contain other active or inactive ingredients.

Therapeutic effect of the compound of the present invention can be determined by standard therapeutic procedures in in vitro assays or experimental animals, e.g., by determining the $ED_{50}$ (the dose therapeutically effective in 50% of the population).

The data obtained from in vitro assays and animal studies can be used in formulating a range of dosage for use in humans. The dosage may vary depending upon the formulation and the route of administration. For any compound used in the method of the invention, the therapeutically effective dose can be estimated initially from in vitro assays or mammalian assays. A dose may be formulated in animal models to achieve a desired circulating plasma concentration range based on these assays. Such information can be used to more accurately determine useful doses in humans. The therapeutically effective dose can also be determined from human data. Levels in plasma may be measured, for example, by high performance liquid chromatography or mass spectrometer.

It is well known to those skilled in the art that certain factors may influence the dosage and timing required to effectively treat a mammal, the factors including, but not limited to, the severity of the disease or disorder, previous treatments, the general health and/or age of the mammal, and other diseases present. Further, the treatment of a mammal with a therapeutically effective amount of the compound of the present invention may include, but not limited to, a single treatment, alternate-day treatment, and a series of treatments.

The precise amount of the compound administered to a human patient will be particularly within the responsibility of the attendant physician. However, the dose employed will depend upon a number of factors including the age and sex of the patient, the precise condition being treated and its severity, and the route of administration.

The compound is conveniently administered in the form of a pharmaceutical composition. Such a composition may conveniently be presented for use in conventional manner in admixture with one or more pharmaceutically acceptable carriers or excipients. Preferably, the pharmaceutical composition is used for the treatment of cancer. The pharmaceutical composition for the treatment of cancer comprising the compound of the present invention is also one aspect of the present invention.

While it is possible for the compound to be administered as a raw chemical, it is preferable to present it as a pharmaceutical formulation. The formulation comprises the compound together with one or more acceptable carriers or diluents therefor and optionally other therapeutic ingredients. The carrier(s) must be acceptable in the sense of being compatible with the other ingredients of the formulation and not deleterious to the recipient thereof.

A pharmaceutical composition is formulated to meet the desirable route of administration. The administration route is, for example, parenteral (e.g. intravenous, intracutaneous, subcutaneous), oral (e.g. ingestion or inhalation), percutaneous (local), mucosal, rectal, and local (including percutaneous, buccal, and sublingual) administration. The solution or suspension can be prepared by the method described in Remington's Pharmaceutical Sciences (18$^{th}$ ed., Gennaro, ed., Mack Publishing Co., Easton, Pa., (1990)).

The invention also includes combining separate pharmaceutical compositions in a kit form. The kit comprises two or more separate pharmaceutical compositions: the compound of the present invention; and a second active agent as described herein. The kit usually comprises a container for containing the separate compositions such as a divided bottle and a divided foil packet, however, the separate compositions may also be contained within a single, undivided container. The kit form is particularly advantageous when the separate components are preferably administered in different dosage forms (e.g., oral and parenteral), or are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably, the strength of the sheet is such that the tablets or capsules can be removed from the blister pack by manually applying pressure on the recesses whereby an opening is formed in the sheet at the place of the recess. The tablet or capsule can then be removed via said opening.

Exemplary Methods of Combination Therapy

In certain embodiments, the methods provided herein comprise administering the compound of the present invention in combination with one or more second active agents, and/or in combination with surgery. The administration of the compound of the present invention and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. Recommended routes of administration for the second active agents are known to those of ordinary skill in the art. See, e.g., Physicians' Desk Reference.

In one embodiment, the compound of the present invention or the second active agent is administered intravenously or subcutaneously once or twice daily in an amount of from about 0.1 to about 3,000 mg, preferably from about 1 to about 1,000 mg, more preferably from about 5 to about 500 mg, further preferably from about 10 to about 375 mg, most preferably from about 50 to about 200 mg.

In another embodiment, provided herein are methods of treating, preventing and/or managing cachexia, which comprise administering the compound of the present invention in combination with (e.g., before, during or after) conventional therapy including, but not limited to, other non-drug based therapy presently used to treat, prevent or manage cachexia which develops in chronic diseases such as malignant tumor, tuberculosis, diabetes, hemodyscrasia, endocrine disease, chronic obstructive pulmonary disease, chronic kidney disease, cardiac failure, infectious disease, and acquired immunodeficiency syndrome. Without being limited by theory, it is believed that the compound of the present invention may provide additive or synergistic effects when given concurrently with such conventional therapy.

In certain embodiments, the second active agent is co-administered with the compound of the present invention or administered with, in general, approximate 1 to 50 hour delay. In certain embodiments, the compound of the present invention is administered first followed by administration of the second active agent with, in general, approximate 1 to 50 hour delay. In other embodiments, the second active agent is administered first followed by administration of the compound of the present invention with, in general, approximate 1 to 50 hour delay. In some embodiments, the delay is preferably 24 hours.

In one embodiment, the compound of the present invention can be usually administered in a daily amount of from about 0.1 to about 3000 mg alone or in combination with a second active agent disclosed herein, prior to, during, or after the use of conventional therapy.

In another embodiment, the methods provided herein comprise: a) administering to a patient in need thereof, a daily dose of about 0.1 mg to 3000 mg of the compound of the present invention and b) administering a therapeutically effective amount of a second active agent such as a supportive care agent.

The administration mode of the compound of the present invention and a concomitant medicament are not particularly limited, provided that the compound of the present invention and the concomitant medicament are combined upon administration. Such an administration mode may, for example, be (1) an administration of a single formulation obtained by simultaneously formulating the compound of the present invention and a concomitant medicament, (2) a simultaneous administration, via an identical route, of two formulations obtained by separately formulating the compound of the present invention and a concomitant medicament, (3) a time-delayed administration, via an identical route, of two formulations obtained by separately formulating the compound of the present invention and a concomitant medicament, (4) a simultaneous administration, via different routes, of two formulations obtained by separately formulating the compound of the present invention and a concomitant medicament, (5) a time-delayed administration, via different routes, of two formulations obtained by separately formulating the compound of the present invention and a concomitant medicament (for example, administration of the compound of the present invention followed by administration of a concomitant medicament, or inverse order) and the like.

When the compound of the present invention is used in combination with one or more second therapeutic agents (the second active agents), the compound may be administered either sequentially or simultaneously by any convenient route.

The combinations referred to above may conveniently be presented for use in the form of a pharmaceutical formulation and thus use of a pharmaceutical formulation comprising such a combination as defined above together with a pharmaceutically acceptable carrier or excipient is a further aspect of the invention. The individual components of such combinations may be administered either sequentially or simultaneously in separate or combined pharmaceutical formulations.

When the compound of the present invention is used in combination with a second therapeutic agent active against the same disease, the dose of each compound may differ from that when the compound is used alone. Appropriate doses will be readily appreciated by those skilled in the art.

Similarly, it is clear for those skilled in the art that when the compound of the present invention is used in combination with a second therapeutic agent active against the same disease, the dose of each compound may differ from that when the compound is used alone and appropriate doses can be determined by those skilled in the art.

Preferred unit dosage formulations are those containing an effective daily dose, or an appropriate fraction thereof, of the active ingredient. For example, a proposed daily dosage of compound of the present invention may be preferably from about 0.1 mg to 3000 mg, and more preferably about 1 mg to 1000 mg per day. As described before, dosage can be changed by the individual patient, and thus not limited to these.

The subjects to which the compound of the invention or a pharmaceutical composition comprising said compound is to be administered is preferably a mammalian subject including a human. Preferred among these is a mammal which is diagnosed with cachexia which develops in chronic diseases such as malignant tumor, tuberculosis, diabetes, hemodyscrasia, endocrine disease, chronic obstructive pulmonary disease, chronic kidney disease, cardiac failure, infectious disease, and acquired immunodeficiency syndrome.

EXAMPLES

Compound A: 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide Compound B: 2-amino-N-[1-(R)-(2,4-difluoro-benzyloxymethyl)-2-oxo-2-(3-oxo-3a-(R)-pyridin-2-ylmethyl-2-(2,2,2-trifluoro-ethyl)-2,3,3a,4,6,7-hexahydro-pyrazolo[4,3-c]pyridin-5-yl)-ethyl]-2-methyl-propionamide Example 1

Inhibitory Effect on Weight Loss of Tumor-Bearing Mice

Tumor-bearing mice prepared using a murine colon cancer cell line, colon 26, are known to closely reproduce the symptoms of cancer cachexia (Cancer Research, 50, 4528-4532 (1990)). In this experiment, using tumor-bearing mice prepared using a murine colon cancer cell line, CT26, that was established in the same method as that for producing the murine colon cancer cell line, colon 26, (The Journal of Immunology, 154, 4685-4692 (1995)), Compound A of the present invention was evaluated for effects on the body weights of said mice. That is, CT26 colon cancer cells ($5 \times 10^6$) were subcutaneously transplanted in the flank of BALB/c mice at 7 weeks of age. The transplanted mice were divided into two groups, and once every day from the following day of the transplantation, water for injection was orally administered to the control group, whereas Compound A was orally administered at a dose of 75 mg/kg to the compound administration group. The administered volume was 10 mg/kg. Five and ten days after the transplantation, the tumor size (major axis and minor axis) in each mouse was measured, and the tumor volume was calculated from the following formula: (major axis)×(minor axis)$^2$/2. In addition, the body weight of each mouse was measured daily after the transplantation. The tumor volume 5 and 10 days after the transplantation of the CT26 murine colon cancer cells, and the body weight 10 days after the transplantation are shown in Table 1. Data are expressed as the mean±standard error.

TABLE 1

|  | Tumor volume 5 days after transplantation (mm$^3$) | Tumor volume 10 days after transplantation (mm$^3$) | Body weight 10 days after transplantation (g) |
| --- | --- | --- | --- |
| Control group | 130 ± 6 | 285 ± 26 | 20.0 ± 0.4 |
| Compound administration group | 137 ± 8 | 291 ± 25 | 22.3 ± 0.2 |

Results

In the control group, the tumor grew gradually, and the tumor volume 10 days after the transplantation was 285±26 mm$^3$. The tumor volume of the compound administration group was 291±25 mm$^3$, and no significant difference was observed in the tumor volume change in comparison with the control group. Therefore, this results of comparison between the compound administration group and the control group show that Compound A is not capable of reducing the tumor volume.

Prior to the transplantation, no significant difference was observed in the body weight between the compound administration group. However, it was revealed that administration of Compound A to the tumor-bearing mice prepared by transplanting the CT26 murine colon cancer cells significantly increased the body weight of the mice 10 days after the transplantation, in comparison with the control group. This fact is supported by the critical ratio of 0.1% or lower, which shows statistically significant differences between the control group and the composition administration group.

These results indicate that Compound A is useful as a therapeutic agent or improving agent for cachexia.

Example 2

Inhibitory Effect on Weight Loss of Rats with Transplanted Cancer

Animals with transplanted cancer cells or cancer tissue exhibit weight loss and decrease in food consumption, and thus used as an animal model of cancer cachexia ("Endocrinology", 148, 3004-3012, 2007). The effect of Compound A was examined using this model. Sarcoma cells induced by methylcholanthrene were subcutaneously injected into the abdomen of rats. The rats were reared in a normal environment for about eight days and in this way animals used to provide cancer were produced. An amount of 0.2 to 0.3 g of fresh cancer tissue obtained from the animals used to provide cancer was subcutaneously transplanted into the abdomen of rats under anesthesia. From 6 days to 7 days after the transplantation of the cancer, Compound A was administered once a day for 5 days to 14 days, and the body weight was daily measured. Compound A significantly inhibited the progression of the weight loss, which is an indicator for the development of cachexia, in the tumor-bearing animals in a dose-dependent manner.

An experiment was conducted on Compound B in the same manner as described above. As is the case in Compound A, Compound B significantly inhibited the progression of the weight loss, which is an indicator for the development of cachexia, in the tumor-bearing animals in a dose-dependent manner.

INDUSTRIAL APPLICABILITY

The compounds of the present invention can be used for the improvement or treatment of cachexia.

The invention claimed is:

1. A method for inhibiting the progression of weight loss in an animal with cachexia and having a malignant tumor, which comprises:

a) diagnosing an animal with cachexia and having a malignant tumor, and
b) orally administering to the animal with cachexia and having a malignant tumor an effective amount of 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide or a pharmaceutically acceptable salt thereof, to inhibit the progression of weight loss, without contributing to the malignant tumor growth.

2. The method according to claim 1, further comprising administering the 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide or a pharmaceutically acceptable salt thereof in combination with at least one second active agent, wherein the second active agent is at least one selected from the group consisting of a chemotherapeutic agent, an immunotherapeutic agent, and a diuretic agent.

3. The method according to claim 1, wherein the effective amount of 2-amino-N-[2-(3 a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide or a pharmaceutically acceptable salt thereof is orally administered to the animal in a dosage range of 0.01 to 5.0 mg/kg of body weight daily.

4. The method according to claim 1, wherein the animal is selected from the group consisting of a mouse, a rat, a rabbit, a dog, a cat, a bovine, a horse, a pig, and a monkey.

5. The method according to claim 1, wherein the animal is selected from the group consisting of a dog and a cat.

6. The method according to claim 2, wherein the second active agent is administered intravenously or subcutaneously once or twice daily in an amount of from about 0.1 to about 3,000 mg.

7. The method according to claim 2, wherein the second active agent is co-administered with the 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide or a pharmaceutically acceptable salt thereof.

8. The method according to claim 2, wherein the second active agent is administered with approximate 1 to 50 hour delay with the administration of the 2-amino-N-[2-(3a-(R)-benzyl-2-methyl-3-oxo-2,3,3a,4,6,7-hexahydro-pyrazolo[4,3-c]pyridin-5-yl)-1-(R)-benzyloxymethyl-2-oxo-ethyl]-isobutyramide or a pharmaceutically acceptable salt thereof.

* * * * *